(12) United States Patent
Forsell

(10) Patent No.: US 8,965,525 B2
(45) Date of Patent: Feb. 24, 2015

(54) METHOD AND APPARATUS FOR SUPPLYING ENERGY TO A MEDICAL DEVICE

(71) Applicant: Peter Forsell, Bouveret (CH)

(72) Inventor: Peter Forsell, Bouveret (CH)

(*) Notice: Subject to any disclaimer, the term of this patent is extended or adjusted under 35 U.S.C. 154(b) by 0 days.

(21) Appl. No.: 14/338,501

(22) Filed: Jul. 23, 2014

(65) Prior Publication Data
US 2014/0336679 A1 Nov. 13, 2014

Related U.S. Application Data

(63) Continuation of application No. 13/905,384, filed on May 30, 2013, which is a continuation of application No. 12/682,835, filed as application No. PCT/SE2008/000561 on Oct. 10, 2008, now Pat. No. 8,463,395.

(60) Provisional application No. 60/960,832, filed on Oct. 16, 2007, provisional application No. 60/960,861, filed on Oct. 17, 2007.

(51) Int. Cl.
*A61N 1/00* (2006.01)
*A61N 1/378* (2006.01)
*A61B 17/12* (2006.01)
*H02J 7/02* (2006.01)
*H02J 7/12* (2006.01)
*H02J 7/00* (2006.01)
*H02J 7/34* (2006.01)

(52) U.S. Cl.
CPC .............. *A61N 1/3787* (2013.01); *A61B 17/12* (2013.01); *H02J 7/025* (2013.01); *H02J 7/12* (2013.01); *H02J 2007/0059* (2013.01); *H02J 7/345* (2013.01)
USPC .................................. 607/61; 607/60; 607/33

(58) Field of Classification Search
CPC ........ A61N 1/3787; A61N 1/08; A61N 1/378
USPC ................................................ 607/61, 60, 33
See application file for complete search history.

(56) References Cited

U.S. PATENT DOCUMENTS 4,679,560 A 7/1987 Galbraith
5,591,212 A 1/1997 Keimel
(Continued)

FOREIGN PATENT DOCUMENTS

EP 1 513 241 3/2005
EP 1 609 501 12/2005
(Continued)

OTHER PUBLICATIONS

U.S. Appl. No. 13/905,384, Forsell, filed May 30, 2013.
(Continued)

*Primary Examiner* — Christopher D Koharski
*Assistant Examiner* — Philip Edwards

(57) ABSTRACT

In a method and apparatus for supplying wireless energy to a medical device implanted in a patient, wireless energy is transmitted from an external energy source located outside a patient and is received by an internal energy receiver located inside the patient, for directly or indirectly supplying received energy to the medical device. An energy balance is determined between the energy received by the internal energy receiver and the energy used for the medical device, and the transmission of wireless energy is then controlled based on the determined energy balance. The energy balance thus provides an accurate indication of the correct amount of energy needed, which is sufficient to operate the medical device properly, but without causing undue temperature rise.

21 Claims, 13 Drawing Sheets

(56) References Cited

U.S. PATENT DOCUMENTS

| | | |
|---|---|---|
| 5,702,431 A | 12/1997 | Wang et al. |
| 5,713,939 A | 2/1998 | Nedungadi et al. |
| 5,735,887 A | 4/1998 | Barreras, Sr. et al. |
| 5,876,425 A | 3/1999 | Gord et al. |
| 6,442,434 B1 | 8/2002 | Zarinetchi et al. |
| 6,745,077 B1 | 6/2004 | Griffith et al. |
| 6,772,011 B2 | 8/2004 | Dolgin |
| 8,463,394 B2 | 6/2013 | Forsell |
| 8,463,395 B2 | 6/2013 | Forsell |
| 2004/0039423 A1 | 2/2004 | Dolgin |
| 2005/0075697 A1 | 4/2005 | Olson et al. |
| 2006/0030887 A1 | 2/2006 | Letort et al. |
| 2007/0156204 A1 | 7/2007 | Denker et al. |
| 2010/0211133 A1 | 8/2010 | Forsell |
| 2010/0211134 A1 | 8/2010 | Forsell |
| 2010/0217352 A1 | 8/2010 | Forsell |
| 2010/0217353 A1 | 8/2010 | Forsell |
| 2010/0222848 A1 | 9/2010 | Forsell |
| 2010/0222849 A1 | 9/2010 | Forsell |
| 2010/0234922 A1 | 9/2010 | Forsell |
| 2011/0193688 A1 | 8/2011 | Forsell |
| 2011/0196452 A1 | 8/2011 | Forsell |
| 2011/0278948 A1 | 11/2011 | Forsell |
| 2011/0301668 A1 | 12/2011 | Forsell |
| 2012/0112556 A1 | 5/2012 | Forsell |
| 2012/0119700 A1 | 5/2012 | Forsell |
| 2014/0152246 A1 | 6/2014 | Forsell |

FOREIGN PATENT DOCUMENTS

| | | |
|---|---|---|
| WO | WO 03/002192 | 1/2003 |
| WO | WO 2004/018037 | 3/2004 |
| WO | WO 2005/084730 | 9/2005 |

OTHER PUBLICATIONS

U.S. Appl. No. 13/384,387, Forsell, filed Jan. 17, 2012.
U.S. Appl. No. 13/384,039, Forsell, filed Jan. 13, 2012.
U.S. Appl. No. 13/130,648, Forsell, filed Aug. 3, 2011.
U.S. Appl. No. 13/130,634, Forsell, filed Aug. 3, 2011.
U.S. Appl. No. 13/123,638, Forsell, filed Apr. 11, 2011.
U.S. Appl. No. 13/123,168, Forsell, filed Apr. 7, 2011.
U.S. Appl. No. 12/738,182, Forsell, filed Apr. 15, 2010.
U.S. Appl. No. 12/682,831, Forsell, filed Apr. 13, 2010.
U.S. Appl. No. 12/682,477, Forsell, filed Apr. 9, 2010.
U.S. Appl. No. 12/682,404, Forsell, filed Apr. 9, 2010.
U.S. Appl. No. 12/682,336, Forsell, filed Apr. 9, 2010.
U.S. Appl. No. 12/682,327, Forsell, filed Apr. 9, 2010.
International Search Report for PCT/SE2008/000561, mailed Feb. 9, 2009.
Written Opinion of the International Searching Authority for PCT/SE2008/000561, mailed Feb. 9, 2009.

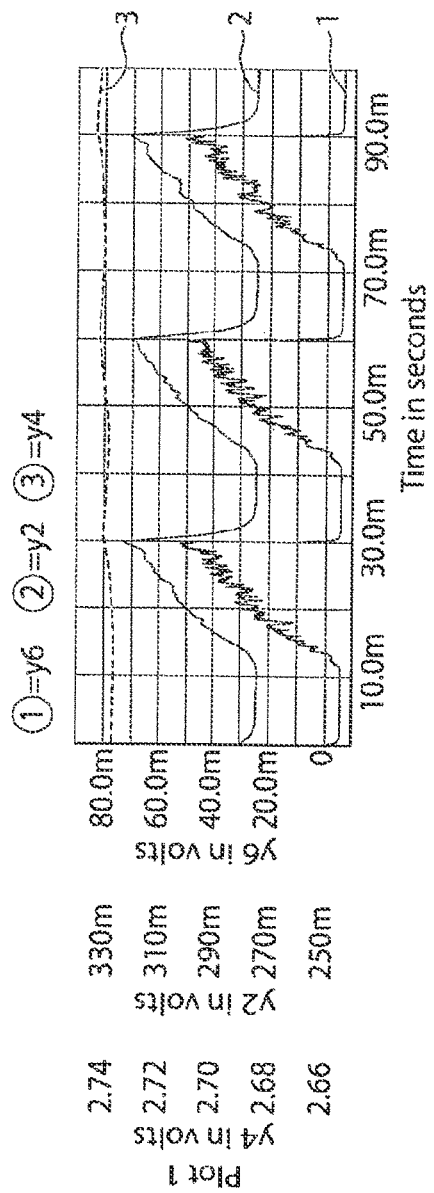

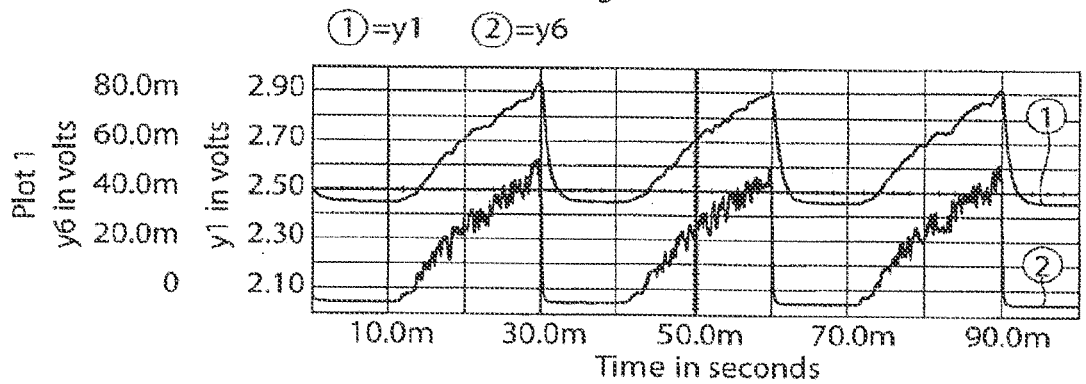
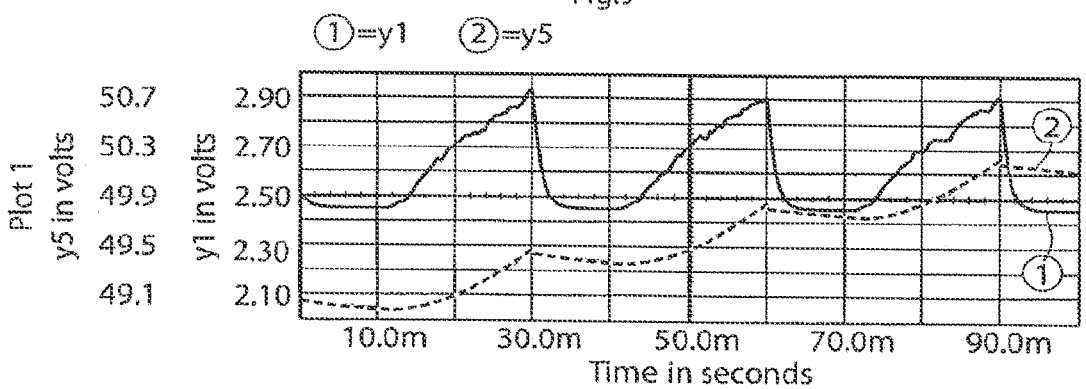
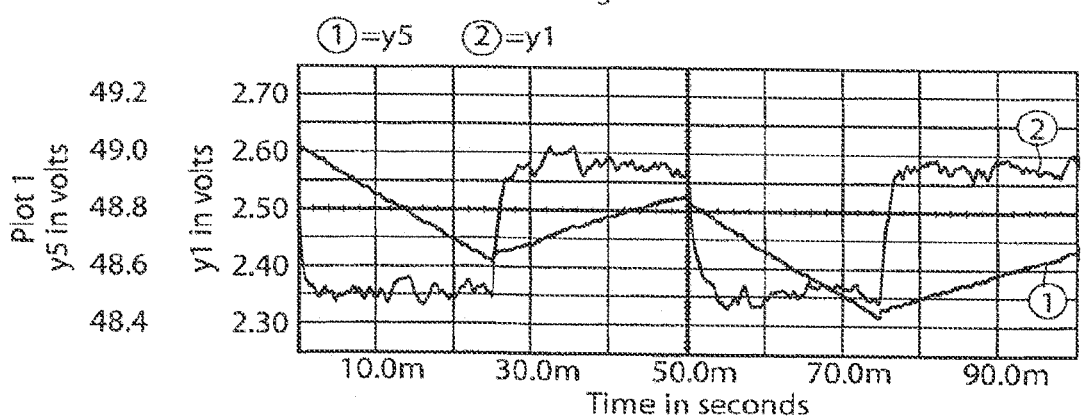

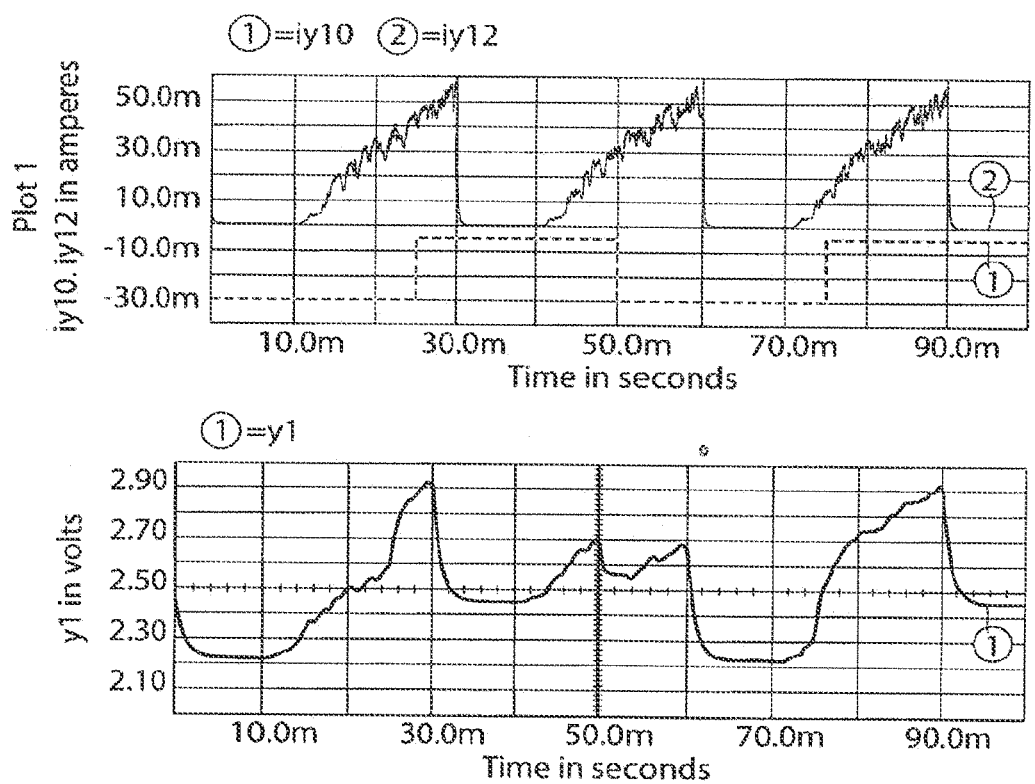

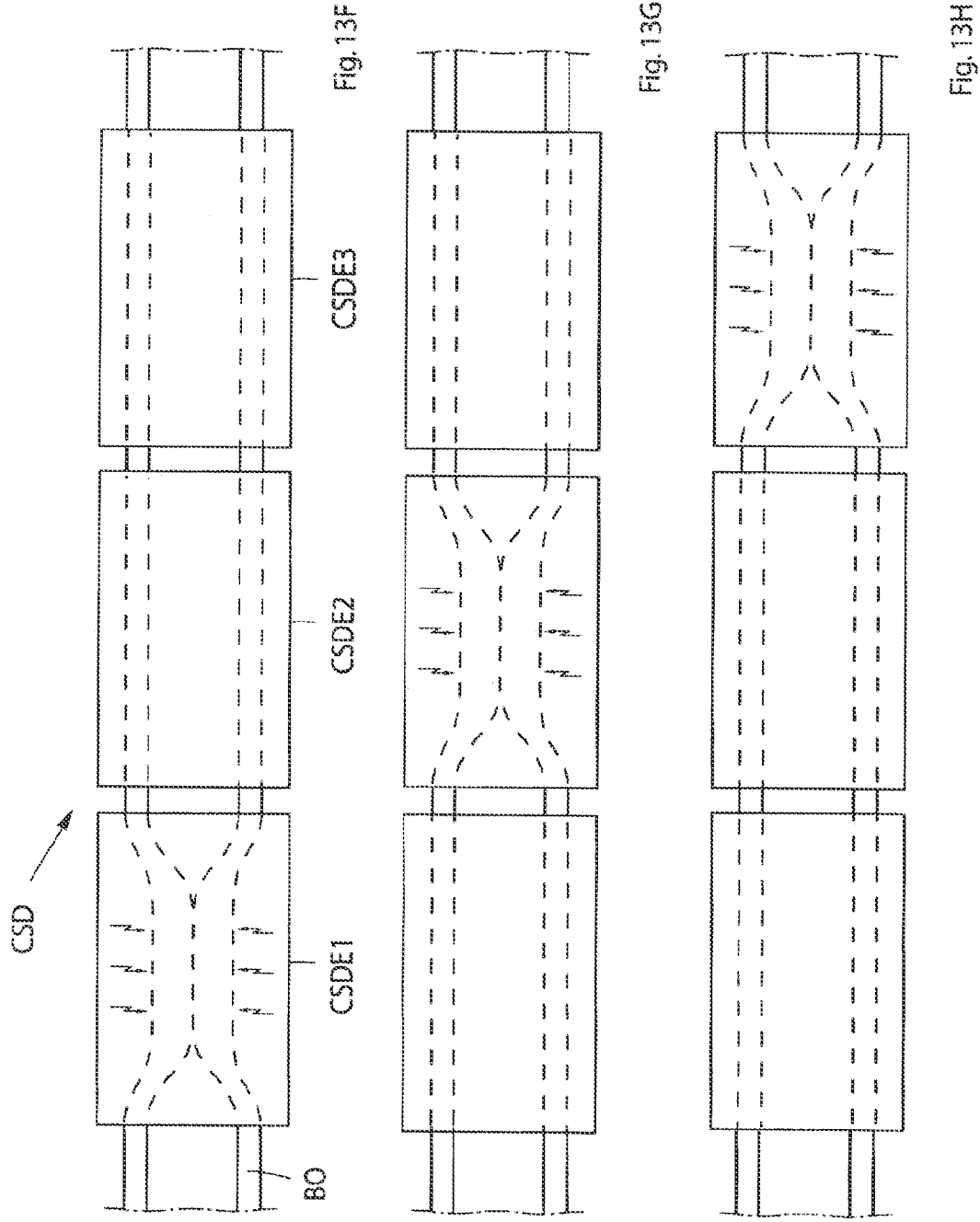

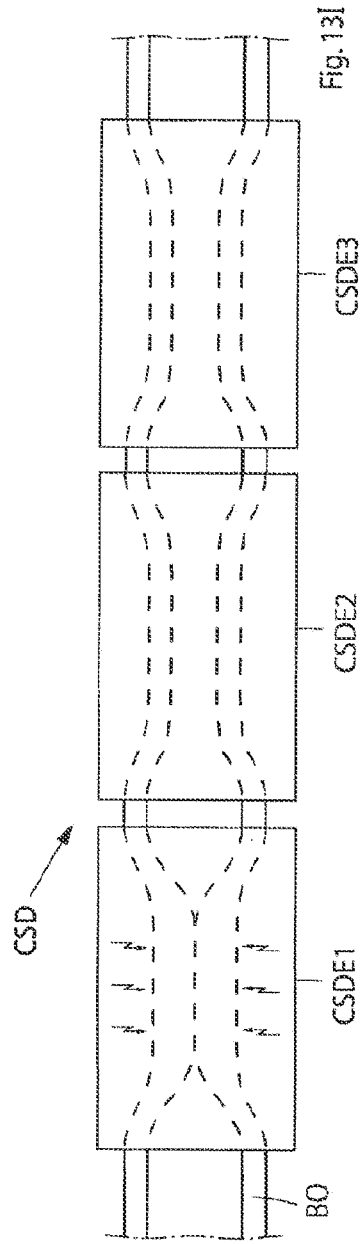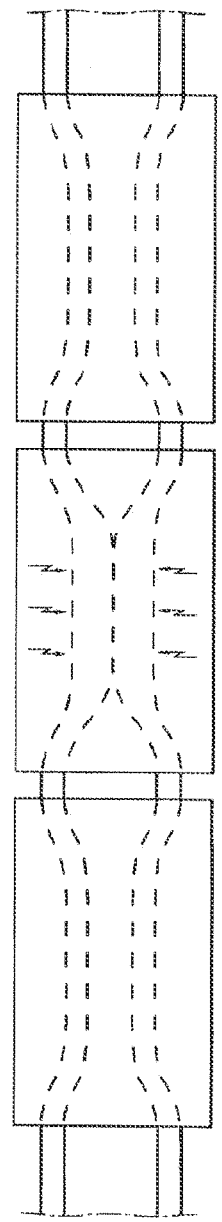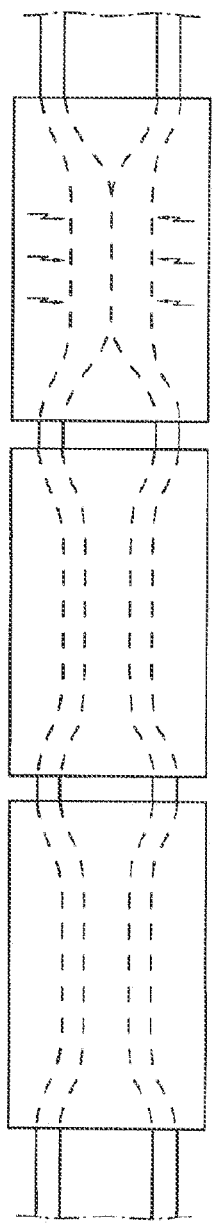

Applied pulses

Applied pulses

METHOD AND APPARATUS FOR SUPPLYING ENERGY TO A MEDICAL DEVICE

This application is a continuation of U.S. application Ser. No. 13/905,384, filed 30 May 2013, which is a continuation of U.S. application Ser. No. 12/682,835, filed 13 Apr. 2010, now U.S. Pat. No. 8,463,395, which is the U.S. national phase of International Application No. PCT/SE2008/000561, filed 10 Oct. 2008, which designated the U.S. and claims the benefit of U.S. Provisional Appln. No. 60/960,832, filed 16 Oct. 2007, and U.S. Provisional Appln. No. 60/960,861, filed 17 Oct. 2007, the entire contents of each of which are incorporated herein by reference.

TECHNICAL FIELD

The present invention relates generally to a method and apparatus for supplying wireless energy to a medical device implanted in a patient. In particular, the invention is concerned with controlling the amount of energy transferred from an energy source outside the patient to an energy receiver inside the patient.

BACKGROUND

Medical devices, designed to be implanted in a patient's body, are typically operated by means of electrical power. Such medical devices include electrical and mechanical stimulators, motors, pumps, etc, which are designed to support or stimulate various body functions. Electrical power can be supplied to such an implanted medical device from a likewise implanted battery or from an external energy source that can supply any needed amount of electrical power intermittently or continuously without requiring repeated surgical operations.

An external energy source can transfer wireless energy to an implanted internal energy receiver located inside the patient and connected to the medical device for supplying received energy thereto. So-called TET (Transcutaneous Energy Transfer) devices are known that can transfer wireless energy in this manner. Thereby, no leads or the like penetrating the skin need to be used for connecting the medical device to an external energy source, such as a battery.

A TET device typically comprises an external energy source including a primary coil adapted to inductively transfer any amount of wireless energy, by inducing voltage in a secondary coil of an internal energy receiver which is implanted preferably just beneath the skin of a patient. The highest transfer efficiency is obtained when the primary coil is positioned close to the skin adjacent to and in alignment with the secondary coil, i.e. when a symmetry axis of the primary coil is parallel to that of the secondary coil.

Typically, the amount of energy required to operate an implanted medical device may vary over time depending on the operational characteristics of the device For example, the device may be designed to switch on and off at certain intervals, or otherwise change its behavior, in order to provide a suitable electrical or mechanical stimulation, or the like. Such operational variations will naturally result in corresponding variations with respect to the amount of required energy.

Furthermore, the position of the external energy source relative to the implanted internal energy receiver is a factor that affects the efficiency of the energy transfer, which highly depends on the distance and relative angle between the source and the receiver. For example, when primary and secondary coils are used, changes in coil spacing result in a corresponding variation of the induced voltage. During operation of the medical device, the patient's movements will typically change the relative spacing of the external source and the internal receiver arbitrarily such that the transfer efficiency greatly varies.

If the transfer efficiency becomes low, the amount of energy supplied to the medical device may be insufficient for operating the device properly, so that its action must be momentarily stopped, naturally disturbing the intended medical effect of the device.

On the other hand, the energy supplied to the medical device may also increase drastically, if the relative positions of the external source and the internal receiver change in a way that unintentionally increases the transfer efficiency. This situation can cause severe problems since the implant cannot "consume" the suddenly very high amount of supplied energy. Unused excessive energy must be absorbed in some way, resulting in the generation of heat, which is highly undesirable. Hence, if excessive energy is transferred from the external energy source to the internal energy receiver, the temperature of the implant will increase, which may damage the surrounding tissue or otherwise have a negative effect on the body functions. It is generally considered that the temperature in the body should not increase more than three degrees to avoid such problems.

It is thus highly desirable to always supply the right amount of energy to an implanted medical device, in order to ensure proper operation and/or to avoid increased temperature. Various methods are known for controlling the amount of transferred energy in response to different conditions in the receiving implant. However, the presently available solutions for controlling the wireless transfer of energy to implanted medical devices are lacking in precision in this respect.

For example, U.S. Pat. No. 5,995,874 discloses a TET system in which the amount of transmitted energy from a primary coil is controlled in response to an indication of measured characteristics of a secondary coil, such as load current and voltage. The transmitted energy can be controlled by varying the current and voltage in the primary coil, transmission frequency or coil dimensions. In particular, a change is effected in the saturation point of the magnetic field between the coils, in order to adjust the power transfer efficiency. However, it is not likely that this solution will work well in practice, since a saturation point in the human tissue would not occur, given the magnetic field levels that are possible to use. Moreover, if the energy transmission must be increased considerably, e.g. to compensate for losses due to variations in alignment and/or spacing between the coils, the relatively high radiation generated may be damaging or unhealthy or unpleasant to the patient, as is well known.

An effective solution is thus needed for accurately controlling the amount of transferred energy to an implanted medical device to ensure proper operation thereof. Moreover, excessive energy transfer resulting in raised temperature at the medical device, and/or power surges should be avoided, in order to avoid tissue damages and other unhealthy or unpleasant consequences for the patient.

SUMMARY OF THE INVENTION

A method is thus provided for controlling transmission of wireless energy supplied to an electrically operable medical device implanted in a patient. The wireless energy is transmitted from an external energy source located outside the patient and is received by an internal energy receiver located inside the patient, the internal energy receiver being connected to the medical device for directly or indirectly supplying received energy thereto. An energy balance is determined between the energy received by the internal energy receiver and the energy used for the medical device. the transmission of wireless energy from the external energy source is then controlled based on the determined energy balance.

An apparatus is also provided for controlling transmission of wireless energy supplied to an electrically operable medical device implanted in a patient. The apparatus is adapted to transmit the wireless energy from an external energy source located outside the patient which is received by an internal energy receiver located inside the patient, the internal energy receiver being connected to the medical device for directly or indirectly supplying received energy thereto. The apparatus is further adapted to determine an energy balance between the energy received by the internal energy receiver and the energy used for the medical device, and control the transmission of wireless energy from the external energy source, based on the determined energy balance.

The method and apparatus may be implemented according to different embodiments and features as follows:

The wireless energy may be transmitted inductively from a primary coil in the external energy source to a secondary coil in the internal energy receiver. A change in the energy balance may be detected to control the transmission of wireless energy based on the detected energy balance change. A difference may also be detected between energy received by the internal energy receiver and energy used for the medical device, to control the transmission of wireless energy based on the detected energy difference.

When controlling the energy transmission, the amount of transmitted wireless energy may be decreased if the detected energy balance change implies that the energy balance is increasing, or vice versa. The decrease/increase of energy transmission may further correspond to a detected change rate.

The amount of transmitted wireless energy may further be decreased if the detected energy difference implies that the received energy is greater than the used energy, or vice versa. The decrease/increase of energy transmission may then correspond to the magnitude of the detected energy difference.

As mentioned above, the energy used for the medical device may be consumed to operate the medical device, and/or stored in at least one energy storage device of the medical device.

In one alternative, substantially all energy used for the medical device is consumed (e.g. by the consuming part 200a of FIG. 2) to operate the medical device. In that case, the energy may be consumed after being stabilized in at least one energy stabilizing unit of the medical device.

In another alternative, substantially all energy used for the medical device is stored in the at least one energy storage device. In yet another alternative, the energy used for the medical device is partly consumed to operate the medical device and partly stored in the at least one energy storage device.

The energy received by the internal energy receiver may be stabilized by a capacitor, before the energy is supplied directly or indirectly to the medical device.

The difference between the total amount of energy received by the internal energy receiver and the total amount of consumed and/or stored energy may be directly or indirectly measured over time, and the energy balance can then be determined based on a detected change in the total amount difference.

The energy received by the internal energy receiver may further be accumulated and stabilized in an energy stabilizing unit, before the energy is supplied to the medical device. In that case, the energy balance may be determined based on a detected change followed over time in the amount of consumed and/or stored energy. Further, the change in the amount of consumed and/or stored energy may be detected by determining over time the derivative of a measured electrical parameter related to the amount of consumed and/or stored energy, where the derivative at a first given moment is corresponding to the rate of the change at the first given moment, wherein the rate of change includes the direction and speed of the change. The derivative may further be determined based on a detected rate of change of the electrical parameter.

The energy received by the internal energy receiver may be supplied to the medical device with at least one constant voltage, wherein the constant voltage is created by a constant voltage circuitry. In that case, the energy may be supplied with at least two different voltages, including the at least one constant voltage.

The energy received by the internal energy receiver may also be supplied to the medical device with at least one constant current, wherein the constant current is created by a constant current circuitry. In that case, the energy may be supplied with at least two different currents including the at least one constant current.

The energy balance may also be determined based on a detected difference between the total amount of energy received by the internal energy receiver and the total amount of consumed and/or stored energy, the detected difference being related to the integral over time of at least one measured electrical parameter related to the energy balance. In that case, values of the electrical parameter may be plotted over time as a graph in a parameter-time diagram, and the integral can be determined from the size of the area beneath the plotted graph. The integral of the electrical parameter may relate to the energy balance as an accumulated difference between the total amount of energy received by the internal energy receiver and the total amount of consumed and/or stored energy.

The energy storage device in the medical device may include at least one of: a rechargeable battery, an accumulator or a capacitor. The energy stabilizing unit may include at least one of: an accumulator, a capacitor or a semiconductor adapted to stabilize the received energy.

When the energy received by the internal energy receiver is accumulated and stabilized in an energy stabilizing unit before energy is supplied to the medical device and/or energy storage device, the energy may be supplied to the medical device and/or energy storage device with at least one constant voltage, as maintained by a constant voltage circuitry. In that case, the medical device and energy storage device may be supplied with two different voltages, wherein at least one voltage is constant, maintained by the constant voltage circuitry.

Alternatively, when the energy received by the internal energy receiver is accumulated and stabilized in an energy stabilizing unit before energy is supplied to the medical device and/or energy storage device, the energy may be supplied to the medical device and/or energy storage device with at least one constant current, as maintained by a constant current circuitry. In that case, the medical device and energy storage device may be supplied with two different currents wherein at least one current is constant, maintained by the constant current circuitry.

The wireless energy may be initially transmitted according to a predetermined energy consumption plus storage rate. In that case, the transmission of wireless energy may be turned off when a predetermined total amount of energy has been transmitted. The energy received by the internal energy receiver may then also be accumulated and stabilized in an energy stabilizing unit before being consumed to operate the medical device and/or stored in the energy storage device until a predetermined total amount of energy has been consumed and/or stored.

Further, the wireless energy may be first transmitted with the predetermined energy rate, and then transmitted based on the energy balance which can be determined by detecting the total amount of accumulated energy in the energy stabilizing unit. Alternatively, the energy balance can be determined by detecting a change in the current amount of accumulated energy in the energy stabilizing unit. In yet another alternative, the energy balance, can be determined by detecting the direction and rate of change in the current amount of accumulated energy in the energy stabilizing unit.

The transmission of wireless energy may be controlled such that an energy reception rate in the internal energy receiver corresponds to the energy consumption and/or storage rate. In that case, the transmission of wireless energy may be turned off when a predetermined total amount of energy has been consumed.

The energy received by the internal energy receiver may be first accumulated and stabilized in an energy stabilizing unit, and then consumed or stored by the medical device until a predetermined total amount of energy has been consumed. In that case, the energy balance may be determined based on a detected total amount of accumulated energy in the energy stabilizing unit. Alternatively, the energy balance may be determined by detecting a change in the current amount of accumulated energy in the energy stabilizing unit. In yet another alternative, the energy balance may be determined by detecting the direction and rate of change in the current amount of accumulated energy in the energy stabilizing unit. Suitable sensors may be used for measuring certain characteristics of the medical device and/or detecting the current condition of the patient, somehow reflecting the required amount of energy needed for proper operation of the medical device. Thus, electrical and/or physical parameters of the medical device and/or physical parameters of the patient may be determined, and the energy can then be transmitted with a transmission rate which is determined based on the parameters. Further, the transmission of wireless energy may be controlled such that the total amount of transmitted energy is based on said parameters.

The energy received by the internal energy receiver may be first accumulated and stabilized in an energy stabilizing unit, and then consumed until a predetermined total amount of energy has been consumed. The transmission of wireless energy may further be controlled such that an energy reception rate at the internal energy receiver corresponds to a predetermined energy consumption rate.

Further, electrical and/or physical parameters of the medical device and/or physical parameters of the patient may be determined, in order to determine the total amount of transmitted energy based on the parameters. In that case, the energy received by the internal energy receiver may be first accumulated and stabilized in an energy stabilizing unit, and then consumed until a predetermined total amount of energy has been consumed.

The energy is stored in the energy storage device according to a predetermined storing rate. The transmission of wireless energy may then be turned off when a predetermined total amount of energy has been stored. The transmission of wireless energy can be further controlled such that an energy reception rate at the internal energy receiver corresponds to the predetermined storing rate.

The energy storage device of the medical device may comprise a first storage device and a second storage device, wherein the energy received by the internal energy receiver is first stored in the first storage device, and the energy is then supplied from the first storage device to the second storage device at a later stage.

When using the first and second storage devices in the energy storage device, the energy balance may be determined in different ways. Firstly, the energy balance may be determined by detecting the current amount of energy stored in the first storage device, and the transmission of wireless energy may then be controlled such that a storing rate in the second storage device corresponds to an energy reception rate in the internal energy receiver. Secondly, the energy balance may be determined based on a detected total amount of stored energy in the first storage device. Thirdly, the energy balance may be determined by detecting a change in the current amount of stored energy in the first storage device. Fourthly, the energy balance may be determined by detecting the direction and rate of change in the current amount of stored energy in the first storage device.

Stabilized energy may be first supplied from the first storage device to the second storage device with a constant current, as maintained by a constant current circuitry, until a measured voltage over the second storage device reaches a predetermined maximum voltage, and thereafter supplied from the first storage device to the second storage energy storage device with a constant voltage, as maintained by a constant voltage circuitry. In that case, the transmission of wireless energy may be turned off when a predetermined minimum rate of transmitted energy has been reached.

The transmission of energy may further be controlled such that the amount of energy received by the internal energy receiver corresponds to the amount of energy stored in the second storage device. In that case, the transmission of energy may be controlled such that an energy reception rate at the internal energy receiver corresponds to an energy storing rate in the second storage device. The transmission of energy may also be controlled such that a total amount of received energy at the internal energy receiver corresponds to a total amount of stored energy in the second storage device.

In the case when the transmission of wireless energy is turned off when a predetermined total amount of energy has been stored, electrical and/or physical parameters of the medical device and/or physical parameters of the patient may be determined during a first energy storing procedure, and the predetermined total amount of energy may be stored in a subsequent energy storing procedure based on the parameters.

When electrical and/or physical parameters of the medical device and/or physical parameters of the patient are determined, the energy may be stored in the energy storage device with a storing rate which is determined based on the parameters. In that case, a total amount of energy may be stored in the energy storage device, the total amount of energy being determined based on the parameters. The transmission of wireless energy may then be automatically turned off when the total amount of energy has been stored. The transmission of wireless energy may further be controlled such that an energy reception rate at the internal energy receiver corresponds to the storing rate.

When electrical and/or physical parameters of the medical device and/or physical parameters of the patient are determined, a total amount of energy may be stored in the energy storage device, the total amount of energy being determined based on said parameters. The transmission of energy may then be controlled such that the total amount of received energy at the internal energy receiver corresponds to the total amount of stored energy. Further, the transmission of wireless energy may be automatically turned off when the total amount of energy has been stored.

When the energy used for the medical device is partly consumed and partly stored, the transmission of wireless energy may be controlled based on a predetermined energy consumption rate and a predetermined energy storing rate. In that case, the transmission of energy may be turned off when a predetermined total amount of energy has been received for consumption and storage. The transmission of energy may also be turned off when a predetermined total amount of energy has been received for consumption and storage.

When electrical and/or physical parameters of the medical device and/or physical parameters of the patient are determined, the energy may be transmitted for consumption and storage according to a transmission rate per time unit which is determined based on said parameters. The total amount of transmitted energy may also be determined based on said parameters.

When electrical and/or physical parameters of the medical device and/or physical parameters of the patient are determined, the energy may be supplied from the energy storage device to the medical device for consumption with a supply rate which is determined based on said parameters. In that case, the total amount of energy supplied from the energy storage device to the medical device for consumption, may be based on said parameters.

When electrical and/or physical parameters of the medical device and/or physical parameters of the patient are determined, a total amount of energy may be supplied to the medical device for consumption from the energy storage device, where the total amount of supplied energy is determined based on the parameters.

When the energy received by the internal energy receiver is accumulated and stabilized in an energy stabilizing unit, the energy balance may be determined based on an accumulation rate in the energy stabilizing unit, such that a storing rate in the energy storage device corresponds to an energy reception rate in the internal energy receiver.

When a difference is detected between the total amount of energy received by the internal energy receiver and the total amount of consumed and/or stored energy, and the detected difference is related to the integral over time of at least one measured electrical parameter related to said energy balance, the integral may be determined for a monitored voltage and/or current related to the energy balance.

When the derivative is determined over time of a measured electrical parameter related to the amount of consumed and/or stored energy, the derivative may be determined for a monitored voltage and/or current related to the energy balance.

When using the first and second storage devices in the energy storage device, the second storage device may directly or indirectly supply energy to the medical device, wherein the change of the difference corresponds to a change of the amount of energy accumulated in the first storage unit. The energy balance may then be determined by detecting a change over time in the energy storing rate in the first storage device, the energy balance corresponding to the change. The change in the amount of stored energy may also be detected by determining over time the derivative of a measured electrical parameter indicating the amount of stored energy, the derivative corresponding to the change in the amount of stored energy. A rate of change of the electrical parameter may also be detected, the derivative being related to the change rate. The electrical parameter may be a measured voltage and/or current related to the energy balance.

The first storage device may include at least one of: a capacitor and a semiconductor, and the second storage device includes at least one of: a rechargeable battery, an accumulator and a capacitor.

As mentioned above, the wireless energy may be transmitted inductively from a primary coil in the external energy source to a secondary coil in the internal energy receiver. However, the wireless energy may also be transmitted non-inductively. For example, the wireless energy may be transmitted by means of sound or pressure variations, radio or light. The wireless energy may also be transmitted in pulses or waves and/or by means of an electric field.

When the wireless energy is transmitted from the external energy source to the internal energy receiver in pulses, the transmission of wireless energy may be controlled by adjusting the width of the pulses.

When the difference between the total amount of energy received by the internal energy receiver and the total amount of consumed energy is measured over time, directly or indirectly, the energy balance may be determined by detecting a change in the difference. In that case, the change in the amount of consumed energy may be detected by determining over time the derivative of a measured electrical parameter related to the amount of consumed energy, the derivative corresponding to the rate of the change in the amount of consumed energy, wherein the rate of change includes the direction and speed of the change. A rate of change of the electrical parameter may then be detected, the derivative being related to the detected change rate.

When using the first and second storage devices in the energy storage device, the first storage device may be adapted to be charged at a relatively higher energy charging rate as compared to the second storage device, thereby enabling a relatively faster charging. The first storage device may also be adapted to be charged at multiple individual charging occasions more frequently as compared to the second storage device, thereby providing relatively greater life-time in terms of charging occasions. The first storage device may comprise at least one capacitor. Normally, only the first storage may be charged and more often than needed for the second storage device.

When the second storage device needs to be charged, to reduce the time needed for charging, the first storage device is charged at multiple individual charging occasions, thereby leaving time in between the charging occasions for the first storage device to charge the second storage device at a relatively lower energy charging rate. When electrical parameters of the medical device are determined, the charging of the second storage device may be controlled based on the parameters. A constant current or stabilizing voltage circuitry may be used for storing energy in the second storage device.

A System to Control the Wireless Energy Supply Based on the Feed Back System

The transmission of wireless energy from the external energy source may be controlled by applying to the external energy source electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

Thus is provided a method of transmitting wireless energy from an external energy transmitting device placed externally to a human body to an internal energy receiver placed internally in the human body, the method comprising:

applying to the external transmitting device electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

Also is provided an apparatus adapted to transmit wireless energy from an external energy transmitting device placed externally to a human body to an internal energy receiver placed internally in the human body, the apparatus comprising, 5a first electric circuit to supply electrical pulses to the external transmitting device, said electrical pulses having leading and trailing edges, said transmitting device adapted to supply wireless energy, wherein the electrical circuit being adapted to vary the lengths of first time intervals between successive leading and trailing edges of the electrical pulses and/or the lengths of second time intervals between successive trailing and leading edges of the electrical pulses, and wherein the transmitted wireless energy, generated from the electrical pulses having a varied power, the power depending on the lengths of the first and/or second time intervals.

The method and apparatus may be implemented according to different embodiments and features as follows:

In that case, the frequency of the electrical pulses may be substantially constant when varying the first and/or second time intervals. When applying electrical pulses, the electrical pulses may remain unchanged, except for varying the first and/or second time intervals. The amplitude of the electrical pulses may be substantially constant when varying the first and/or second time intervals. Further, the electrical pulses may be varied by only varying the lengths of first time intervals between successive leading and trailing edges of the electrical pulses.

A train of two or more electrical pulses may be supplied in a row, wherein when applying the train of pulses, the train having a first electrical pulse at the start of the pulse train and having a second electrical pulse at the end of the pulse train, two or more pulse trains may be supplied in a row, wherein the lengths of the second time intervals between successive trailing edge of the second electrical pulse in a first pulse train and leading edge of the first electrical pulse of a second pulse train are varied.

When applying the electrical pulses, the electrical pulses may have a substantially constant current and a substantially constant voltage. The electrical pulses may also have a substantially constant current and a substantially constant voltage. Further, the electrical pulses may also have a substantially constant frequency. The electrical pulses within a pulse train may likewise have a substantially constant frequency.

When applying electrical pulses to the external energy source, the electrical pulses may generate an electromagnetic field over the external energy source, the electromagnetic field being varied by varying the first and second time intervals, and the electromagnetic field may induce electrical pulses in the internal energy receiver, the induced pulses carrying energy transmitted to the internal energy receiver.

The wireless energy is then transmitted in a substantially purely inductive way from the external energy source to the internal energy receiver.

The electrical pulses may be released from the first electrical circuit with such a frequency and/or time period between leading edges of the consecutive pulses, so that when the lengths of the first and/or second time intervals are varied, the resulting transmitted energy are varied. When applying the electrical pulses, the electrical pulses may have a substantially constant frequency.

The circuit formed by the first electric circuit and the external energy source may have a first characteristic time period or first time constant, and when effectively varying the transmitted energy, such frequency time period may be in the range of the first characteristic time period or time constant or shorter.

One Embodiment of an Apparatus or Method to be Used with the Energy Feed Back System The wireless energy may be used for controlling a flow of fluid and/or other bodily matter in a lumen formed by a tissue wall of a patient's organ. At least one portion of the tissue wall may then be gently constricted to influence the flow in the lumen, and the constricted wall portion may be stimulated to cause contraction of the wall portion to further influence the flow in the lumen.

The object of the present embodiment is to provide an apparatus adapted to control or a method for controlling the flow of fluids and/or other bodily matter in lumens formed by tissue walls of bodily organs, so as to at least substantially or even completely eliminate the injured tissue wall problems that have resulted from implanted prior art devices that constrict such bodily organs.

In accordance with this object of the present invention, there is provided an apparatus adapted to control or a method for controlling the flow of fluids and/or other bodily matter in a lumen that is formed by the tissue wall of a bodily organ, the apparatus comprising an implantable constriction device for gently constricting a portion of the tissue wall to influence the flow in the lumen, a stimulation device for stimulating the wall portion of the tissue wall, and a control device for controlling the stimulation device to stimulate the wall portion as the constriction device constricts the wall portion to cause contraction of the wall portion to further influence the flow in the lumen.

The present invention provides an advantageous combination of constriction and stimulation devices, which results in a two-stage influence on the flow of fluids and/or other bodily matter in the lumen of a bodily organ. Thus, the constriction device may gently constrict the tissue wall by applying a relatively weak force against the wall portion, and the stimulation device may stimulate the constricted wall portion to achieve the desired final influence on the flow in the lumen. The phrase "gently constricting a portion of the tissue wall" is to be understood as constricting the wall portion without substantially hampering the blood circulation in the tissue wall.

Thus both a method for controlling the flow in the lumen and an apparatus adapted to control the flow in the lumen may be implemented according to different embodiments and features as follows:

Preferably, the stimulation device is adapted to stimulate different areas of the wall portion as the constriction device constricts the wall portion, and the control device controls the stimulation device to intermittently and individually stimulate the areas of the wall portion. This intermittent and individual stimulation of different areas of the wall portion of the organ allows tissue of the wall portion to maintain substantially normal blood circulation during the operation of the apparatus of the invention.

The combination of the constriction and stimulation devices enables application of the apparatus or method of the invention at any place on any kind of bodily organs, in particular, but not limited to, tubular bodily organs, which is a significant advance in the art, as compared with prior stimulation devices that are confined to electric stimulation of malfunctioning sphincters.

In most applications using the present invention, there will be daily adjustments of the implanted constriction device. Therefore, in a preferred embodiment of the invention, the constriction device is adjustable to enable adjustment of the constriction of the wall portion as desired, wherein the control device controls the constriction device to adjust the constriction of the wall portion. The control device may control the constriction and stimulation devices independently of each other, and simultaneously. Optionally, the control device may control the stimulation device to stimulate, or to not stimulate the wall portion while the control device controls the constriction device to change the constriction of the wall portion.

Initially, the constriction device may be calibrated by using the control device to control the stimulation device to stimulate the wall portion, while controlling the constriction device to adjust the constriction of the wall portion until the desired restriction of the flow in the lumen is obtained.

Flow Restriction

The apparatus of the present invention is well suited for restricting the flow of fluids and/or other bodily matter in the lumen of a bodily organ. Thus, in a principal embodiment of the invention, the constriction device is adapted to constrict the wall portion to at least restrict the flow in the lumen, and the control device controls the stimulation device to cause contraction of the constricted wall portion, so that the flow in the lumen is at least further restricted. Specifically, the constriction device is adapted to constrict the wall portion to a constricted state in which the blood circulation in the constricted wall portion is substantially unrestricted and the flow in the lumen is at least restricted, and the control device controls the stimulation device to cause contraction of the wall portion, so that the flow in the lumen is at least further restricted when the wall portion is kept by the constriction device in the constricted state.

The constriction and stimulation devices may be controlled to constrict and stimulate, respectively, to an extent that depends on the flow restriction that is desired to be achieved in a specific application of the apparatus of the invention. Thus, in accordance with a first flow restriction option, the control device controls the constriction device to constrict the wall portion, such that flow in the lumen is restricted or stopped, and controls the stimulation device to stimulate the constricted wall portion to cause contraction thereof, such that flow in the lumen is further restricted or more safely stopped. More precisely, the control device may control the stimulation device in a first mode to stimulate the constricted wall portion to further restrict or stop the flow in the lumen and to;

a) control the stimulation device in a second mode to cease the stimulation of the wall portion to increase the flow in the lumen; or b) control the stimulation and constriction devices in the second mode to cease the stimulation of the wall portion and release the wall portion to restore the flow in the lumen.

Movement of Fluid and/or Other Bodily Matter in Lumen

In one embodiment the constriction device is adapted to constrict the wall portion to restrict or vary the flow in the lumen, and the control device controls the stimulation device to progressively stimulate the constricted wall portion, in the downstream or upstream direction of the lumen, to cause progressive contraction of the wall portion to move the fluid and/or other bodily matter in the lumen.

Stimulation

The control device may control the stimulation device to stimulate one or more of the areas of the wall portion at a time, for example by sequentially stimulating the different areas. Furthermore, the control device may control the stimulation device to cyclically propagate the stimulation of the areas along the wall portion, preferably in accordance with a determined stimulation pattern. To achieve the desired reaction of the tissue wall during the stimulation thereof, the control device may control the stimulation device to, preferably cyclically, vary the intensity of the stimulation of the wall portion.

In a preferred embodiment of the invention, the control device controls the stimulation device to intermittently stimulate the areas of the wall portion with pulses that preferably form pulse trains. At least a first area and a second area of the areas of the wall portion may be repeatedly stimulated with a first pulse train and a second pulse train, respectively, such that the first and second pulse trains over time are shifted relative to each other. For example, the first area may be stimulated with the first pulse train, while the second area is not stimulated with said second pulse train, and vice versa. Alternatively, the first and second pulse trains may be shifted relative to each other, such that the first and second pulse trains at least partially overlap each other.

The pulse trains can be configured in many different ways. Thus, the control device may control the stimulation device to vary the amplitudes of the pulses of the pulse trains, the duty cycle of the individual pulses of each pulse train, the width of each pulse of the pulse trains, the length of each pulse train, the repetition frequency of the pulses of the pulse trains, the repetition frequency of the pulse trains, the number of pulses of each pulse train, and/or the off time periods between the pulse trains. Several pulse trains of different configurations may be employed to achieve the desired effect.

In case the control device controls the stimulation device to vary the off time periods between pulse trains that stimulate the respective area of the wall portion, it is also possible to control each off time period between pulse trains to last long enough to restore substantially normal blood circulation in the area when the latter is not stimulated during the off time periods.

An electric stimulation device suitably comprises at least one, preferably a plurality of electrical elements, such as electrodes, for engaging and stimulating the wall portion with electric pulses. Optionally, the electrical elements may be placed in a fixed orientation relative to one another. The control device controls the electric stimulation device to electrically energize the electrical elements, one at a time, or groups of electrical elements at a time. Preferably, the control device controls the electric stimulation device to cyclically energize each element with electric pulses. Optionally, the control device may control the stimulation device to energize the electrical elements, such that the electrical elements are energized one at a time in sequence, or such that a number or groups of the electrical elements are energized at the same time. Also, groups of electrical elements may be sequentially energized, either randomly or in accordance with a predetermined pattern.

The electrical elements may form any pattern of electrical elements. Preferably, the electrical elements form an elongate pattern of electrical elements, wherein the electrical elements are applicable on the patient's wall of the organ, such that the elongate pattern of electrical elements extends lengthwise along the wall of the organ, and the elements abut the respective areas of the wall portion. The elongate pattern of electrical elements may include one or more rows of electrical elements extending lengthwise along the wall of the organ. Each row of electrical elements may form a straight, helical or zig-zag path of electrical elements, or any form of path. The control device may control the stimulation device to successively energize the electrical elements longitudinally along the elongate pattern of electrical elements in a direction opposite to, or in the same direction as that of, the flow in the patient's lumen.

In accordance with a preferred embodiment of the invention, the electrical elements form a plurality of groups of elements, wherein the groups form a series of groups extending along the patient's organ in the flow direction in the patient's lumen. The electrical elements of each group of electrical elements may form a path of elements extending at least in part around the patient's organ. In a first alternative, the electrical elements of each group of electrical elements may form more than two paths of elements extending on different sides of the patient's organ, preferably substantially transverse to the flow direction in the patient's lumen. The control device may control the stimulation device to energize the groups of electrical elements in the series of groups in random, or in accordance with a predetermined pattern. Alternatively, the control device may control the stimulation device to successively energize the groups of electrical elements in the series of groups in a direction opposite to, or in the same direction as that of, the flow in the patient's lumen, or in both said directions starting from a position substantially at the center of the constricted wall portion. For example, groups of energized electrical elements may form advancing waves of energized electrical elements, as described above; that is, the control device may control the stimulation device to energize the groups of electrical elements, such that energized electrical elements form two waves of energized electrical elements that simultaneously advance from the center of the constricted wall portion in two opposite directions towards both ends of the elongate pattern of electrical elements.

Mechanical Operation

Where the operation device mechanically operates the constriction device of the constriction/stimulation unit, it may be non-inflatable. Furthermore, the operation device may comprise a servo system, which may include a gearbox. The term "servo system" encompasses the normal definition of a servo mechanism, i.e., an automatic device that controls large amounts of power by means of very small amounts of power, but may alternatively or additionally encompass the definition of a mechanism that transfers a weak force acting on a moving element having a long stroke into a strong force acting on another moving element having a short stroke.

Preferably, the operation device operates the constriction device in a non-magnetic and/or non-manual manner. A motor may be operatively connected to the operation device. The operation device may be operable to perform at least one reversible function and the motor may be capable of reversing the function.

Hydraulic Operation

Where the operation device hydraulically operates the constriction device of the constriction/stimulation unit, it includes hydraulic means for adjusting the constriction device.

In an embodiment of the invention, the hydraulic means comprises a reservoir and an expandable/contractible cavity in the constriction device, wherein the operation device distributes hydraulic fluid from the reservoir to expand the cavity, and distributes hydraulic fluid from the cavity to the reservoir to contract the cavity. The cavity may be defined by a balloon of the constriction device that abuts the tissue wall portion of the patient's organ, so that the patient's wall portion is constricted upon expansion of the cavity and released upon contraction of the cavity.

Alternatively, the cavity may be defined by a bellows that displaces a relatively large contraction element of the constriction device, for example a large balloon that abuts the wall portion, so that the patient's wall portion is constricted upon contraction of the bellows and released upon expansion of the bellows. Thus, a relatively small addition of hydraulic fluid to the bellows causes a relatively large increase in the constriction of the wall portion. Such a bellows may also be replaced by a suitably designed piston/cylinder mechanism.

Where the hydraulic means comprises a cavity in the constriction device, the apparatus of the invention can be designed in accordance with the options listed below.

1) The reservoir comprises first and second wall portions, and the operation device displaces the first and second wall portions relative to each other to change the volume of the reservoir, such that fluid is distributed from the reservoir to the cavity, or from the cavity to the reservoir.
   1a) The first and second wall portions of the reservoir are displaceable relative to each other by at least one of a magnetic device, a hydraulic device or an electric control device.
   means.
2) The apparatus comprises a fluid conduit between the reservoir and the cavity, wherein the reservoir forms part of the conduit. The conduit and reservoir and apparatus are devoid of any non-return valve. The reservoir forms a fluid chamber with a variable volume, and distributes fluid from the chamber to the cavity by a reduction in the volume of the chamber and withdraws fluid from the cavity by an expansion of the volume of the chamber. The apparatus further comprises a motor for driving the reservoir, comprising a movable wall of the reservoir for changing the volume of the chamber.

In a special embodiment of the invention, the operation device comprises a reverse servo operatively connected to the hydraulic means. The term "reverse servo" is to be understood as a mechanism that transfers a strong force acting on a moving element having a short stroke into a weak force acting on another moving element having a long stroke; i.e., the reverse function of a normal servo mechanism. Thus, minor changes in the amount of fluid in a smaller reservoir could be transferred by the reverse servo into major changes in the amount of fluid in a larger reservoir. The reverse servo is particularly suited for manual operation thereof.

Design of Control Device

The control device suitably controls the constriction/stimulation unit from outside the patient's body. Preferably, the control device is operable by the patient. For example, the control device may comprise a manually operable switch for switching on and off the constriction/stimulation unit, wherein the switch is adapted for subcutaneous implantation in the patient to be manually or magnetically operated from outside the patient's body. Alternatively, the control device may comprise a hand-held wireless remote control, which is conveniently operable by the patient to switch on and off the constriction/stimulation unit. The wireless remote control may also be designed for application on the patient's body like a wristwatch. Such a wristwatch type of remote control may emit a control signal that follows the patient's body to implanted signal responsive means of the apparatus.

The transmission of wireless energy from the external energy transmitting device may be controlled by applying to the external energy transmitting device electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

Thus is provided a method of controlling transmission of wireless energy, the method further comprising:

applying to the external transmitting device electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

Also is provided an apparatus adapted to transmit wireless energy from an external energy transmitting device placed externally to a human body to an internal energy receiver placed internally in the human body, the apparatus comprising, a first electric circuit to supply electrical pulses to the external transmitting device, said electrical pulses having leading and trailing edges, said transmitting device adapted to supply wireless energy, wherein the electrical circuit being adapted to vary the lengths of first time intervals between successive leading and trailing edges of the electrical pulses and/or the lengths of second time intervals between successive trailing and leading edges of the electrical pulses, and wherein the transmitted wireless energy, generated from the electrical pulses having a varied power, the power depending on the lengths of the first and/or second time intervals.

BRIEF DESCRIPTION OF THE DRAWINGS

The present invention will now be described in more detail and with reference to the accompanying drawings, in which:

FIGS. 4-12 are diagrams illustrating various measurements obtained when implementing the inventive method and apparatus according to the circuit diagram of FIG. 3.

FIGS. 13f-3h illustrate different states of operation of a modification of the general embodiment.

FIGS. 13i-13k illustrate an alternative mode of operation of the modification of the general embodiment.

DETAILED DESCRIPTION OF PREFERRED EMBODIMENTS

Briefly described, wireless energy is transmitted from an external energy source located outside a patient and is received by an internal energy receiver located inside the patient. The internal energy receiver is connected to an electrically operable medical device implanted in the patient, for directly or indirectly supplying received energy to the medical device. An energy balance is determined between the energy received by the internal energy receiver and the energy used for the medical device, and the transmission of wireless energy is then controlled based on the determined energy balance. The energy balance thus provides an accurate indication of the correct amount of energy needed, which is sufficient to operate the medical device properly, but without causing undue temperature rise.

Figure 1:
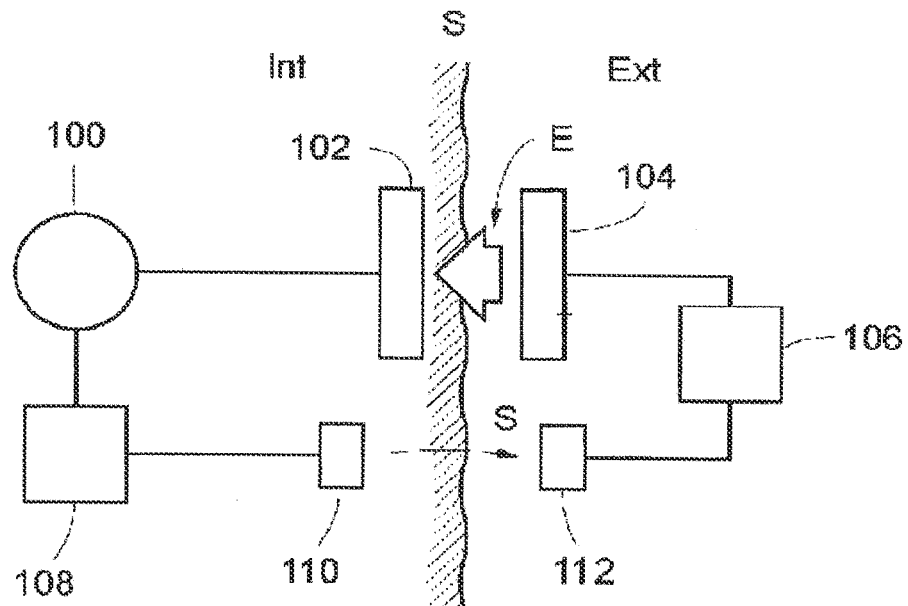
FIG. 1 is a schematic block diagram illustrating an arrangement for supplying an accurate amount of energy to an electrically operable medical device.

In FIG. 1, an arrangement is schematically illustrated for supplying an accurate amount of energy to an electrically operable medical device 100 implanted in a patient, whose skin is indicated by a vertical line S separating the interior "Int" of the patient from the exterior "Ext". The medical device 100 is connected to an internal energy receiver 102, likewise located inside the patient, preferably just beneath the skin S. Generally speaking, the energy receiver 102 may be placed in the abdomen, thorax, muscle fascia (e.g. in the abdominal wall), subcutaneously, or at any other suitable location. The energy receiver 102 is adapted to receive wireless energy E transmitted from an external energy source 104 located outside the skin S in the vicinity of the energy receiver 102.

As is well-known in the art, the wireless energy E may generally be transferred by means of any suitable TET-device, such as a device including a primary coil arranged in the energy source 104 and an adjacent secondary coil arranged in the energy receiver 102. When an electric current is fed through the primary coil, energy in the form of a voltage is induced in the secondary coil which can be used to operate a medical device, e.g. after storing the incoming energy in an energy storing device or accumulator, such as a battery or a capacitor. However, the present invention is generally not limited to any particular energy transfer technique, TET-devices or energy storing devices, and any kind of wireless energy may be used.

The amount of transferred energy can be regulated by means of an external control unit 106 controlling the energy source 104 based on the determined energy balance, as described above. In order to transfer the correct amount of energy, the energy balance and the required amount of energy can be determined by means of an internal control unit 108 connected to the medical device 100. The control unit 108 may thus be arranged to receive various measurements obtained by suitable sensors or the like, not shown, measuring certain characteristics of the medical device 100, somehow reflecting the required amount of energy needed for proper operation of the medical device 100. Moreover, the current condition of the patient may also be detected by means of suitable measuring devices or sensors, in order to provide parameters reflecting the patient's condition. Hence, such characteristics and/or parameters may be related to the current state of the medical device 100, such as power consumption, operational mode and temperature, as well as the patient's condition reflected by, e.g., body temperature, blood pressure, heartbeats and breathing.

Furthermore, an energy storing device or accumulator, not shown here, may also be connected to the energy receiver 102 for accumulating received energy for later use by the medical device 100. Alternatively or additionally, characteristics of such an energy storing device, also reflecting the required amount of energy, may be measured as well. The energy storing device may be a battery, and the measured characteristics may be related to the current state of the battery, such as voltage, temperature, etc. In order to provide sufficient voltage and current to the medical device 100, and also to avoid excessive heating, it is clearly understood that the battery should be charged optimally by receiving a correct amount of energy from the energy receiver 102, i.e. not too little or too much. The energy storing device may also be a capacitor with corresponding characteristics.

For example, battery characteristics may be measured on a regular basis to determine the current state of the battery, which then may be stored as state information in a suitable storage means in the internal control unit 108. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 108 is adapted to determine the energy balance and/or the currently required amount of energy, (either energy per time unit or accumulated energy) based on measurements made by the above-mentioned sensors or measuring devices on the medical device 100, or the patient, or an energy storing device if used, or any combination thereof. The internal control unit 108 is further connected to an internal signal transmitter 110, arranged to transmit a control signal reflecting the determined required amount of energy, to an external signal receiver 112 connected to the external control unit 106. The amount of energy transmitted from the energy source 104 may then be regulated in response to the received control signal.

Alternatively, sensor measurements can be transmitted directly to the external control unit 106 wherein the energy balance and/or the currently required amount of energy can be determined by the external control unit 106, thus integrating the above-described function of the internal control unit 108 in the external control unit 106. In that case, the internal control unit 108 can be omitted and the sensor measurements are supplied directly to the signal transmitter 110 which sends the measurements over to the receiver 112 and the external control unit 106. The energy balance and the currently required amount of energy can then be determined by the external control unit 106 based on those sensor measurements.

Hence, the present solution employs the feed back of information indicating the required energy, which is more efficient than previous solutions because it is based on the actual use of energy that is compared to the received energy, e.g. with respect to the amount of energy, the energy difference, or the energy receiving rate as compared to the energy rate used by the medical device. The medical device may use the received energy either for consuming or for storing the energy in an energy storage device or the like. The different parameters discussed above would thus be used if relevant and needed and then as a tool for determining the actual energy balance. However, such parameters may also be needed per se for any actions taken internally to specifically operate the medical device.

The internal signal transmitter 110 and the external signal receiver 112 may be implemented as separate units using suitable signal transfer means, such as radio, IR (Infrared) or ultrasonic signals. Alternatively, the signal transmitter 110 and the signal receiver 112 may be integrated in the internal energy receiver 102 and the energy source 104, respectively, so as to convey control signals in a reverse direction relative to the energy transfer, basically using the same transmission technique. The control signals may be modulated with respect to frequency, phase or amplitude.

To conclude, the energy supply arrangement illustrated in FIG. 1 may operate basically in the following manner. The energy balance is first determined by the internal control unit 108. A control signal S reflecting the required amount of energy is also created by the internal control unit 108, and the control signal S is transmitted from the signal transmitter 110 to the signal receiver 112. Alternatively, the energy balance can be determined by the external control unit 106 instead depending on the implementation, as mentioned above. In that case, the control signal S may carry measurement results from various sensors. The amount of energy emitted from the energy source 104 can then be regulated by the external control unit 106, based on the determined energy balance, e.g. in response to the received control signal S. This process may be repeated intermittently at certain intervals during ongoing energy transfer, or may be executed on a more or less continuous basis during the energy transfer.

The amount of transferred energy can generally be regulated by adjusting various transmission parameters in the energy source 104, such as voltage, current, amplitude, wave frequency and pulse characteristics.

Figure 2:
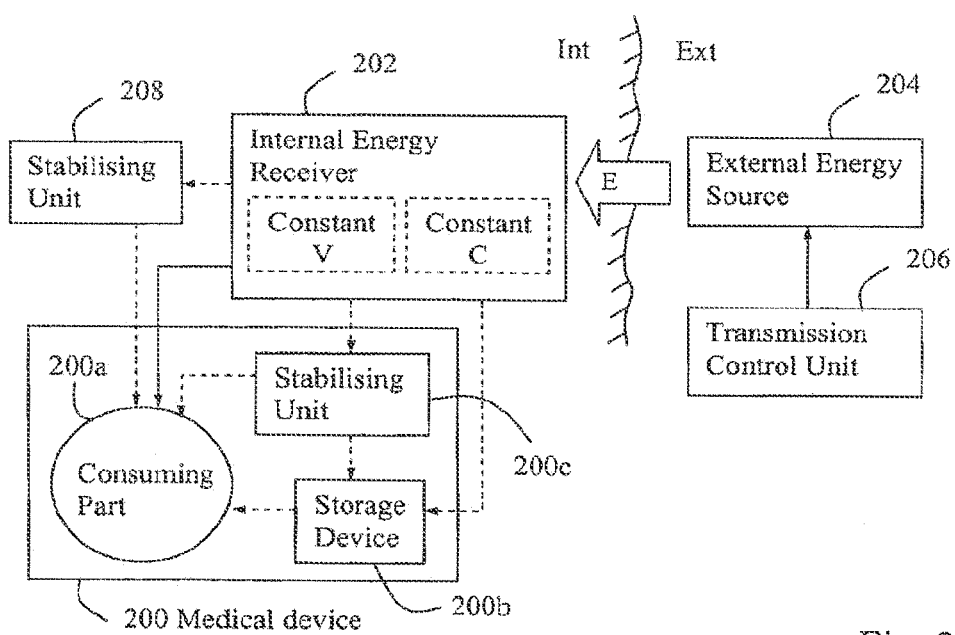
FIG. 2 is a more detailed block diagram of an apparatus for controlling transmission of wireless energy supplied to an electrically operable medical device implanted in a patient.

FIG. 2 illustrates different embodiments for how received energy can be supplied to and used by a medical device 200. Similar to the example of FIG. 1, an internal energy receiver 202 receives wireless energy E from an external energy source 204 which is controlled by a transmission control unit 206. The internal energy receiver 202 may comprise a constant voltage circuit, indicated as a dashed box "constant V" in the figure, for supplying energy at constant voltage to the medical device 200. The internal energy receiver 202 may further comprise a constant current circuit, indicated as a dashed box "constant C" in the figure, for supplying energy at constant current to the medical device 200.

The medical device 200 comprises an energy consuming part 200a which may be a motor, pump, restriction device, or any other medical appliance that requires energy for its electrical operation. The medical device 200 may further comprise an energy storage device 200b for storing energy supplied from the internal energy receiver 202. Thus, the supplied energy may be directly consumed by the energy consuming part 200a or stored by the energy storage device 200b, or the supplied energy may be partly consumed and partly stored. The medical device 200 may further comprise an energy stabilizing unit 200c for stabilizing the energy supplied from the internal energy receiver 202. Thus, the energy may be supplied in a fluctuating manner such that it may be necessary to stabilize the energy before consumed or stored.

The energy supplied from the internal energy receiver 202 may further be accumulated and/or stabilized by a separate energy stabilizing unit 208 located outside the medical device 200, before being consumed and/or stored by the medical device 200. Alternatively, the energy stabilizing unit 208 may be integrated in the internal energy receiver 202. In either case, the energy stabilizing unit 208 may comprise a constant voltage circuit and/or a constant current circuit.

It should be noted that FIG. 1 and FIG. 2 illustrate some possible but non-limiting implementation options regarding how the various shown functional components and elements can be arranged and connected to each other. However, the skilled person will readily appreciate that many variations and modifications can be made within the scope of the present invention.

A method is thus provided for controlling transmission of wireless energy supplied to an electrically operable medical device implanted in a patient. The wireless energy is transmitted from an external energy source located outside the patient and is received by an internal energy receiver located inside the patient, the internal energy receiver being connected to the medical device for directly or indirectly supplying received energy thereto. An energy balance is determined between the energy received by the internal energy receiver and the energy used for the medical device. the transmission of wireless energy from the external energy source is then controlled based on the determined energy balance.

An apparatus is also provided for controlling transmission of wireless energy supplied to an electrically operable medical device implanted in a patient. The apparatus is adapted to transmit the wireless energy from an external energy source located outside the patient which is received by an internal energy receiver located inside the patient, the internal energy receiver being connected to the medical device for directly or indirectly supplying received energy thereto. The apparatus is further adapted to determine an energy balance between the energy received by the internal energy receiver and the energy used for the medical device, and control the transmission of wireless energy from the external energy source, based on the determined energy balance.

The method and apparatus may be implemented according to different embodiments and features as follows.

The wireless energy may be transmitted inductively from a primary coil in the external energy source to a secondary coil in the internal energy receiver. A change in the energy balance may be detected to control the transmission of wireless energy based on the detected energy balance change. A difference may also be detected between energy received by the internal energy receiver and energy used for the medical device, to control the transmission of wireless energy based on the detected energy difference, When controlling the energy transmission, the amount of transmitted wireless energy may be decreased if the detected energy balance change implies that the energy balance is increasing, or vice versa. The decrease/increase of energy transmission may further correspond to a detected change rate.

The amount of transmitted wireless energy may further be decreased if the detected energy difference implies that the received energy is greater than the used energy, or vice versa. The decrease/increase of energy transmission may then correspond to the magnitude of the detected energy difference.

As mentioned above, the energy used for the medical device may be consumed to operate the medical device, and/or stored in at least one energy storage device of the medical device.

In one alternative, substantially all energy used for the medical device is consumed (e.g. by the consuming part 200a of FIG. 2) to operate the medical device. In that case, the energy may be consumed after being stabilized in at least one energy stabilizing unit of the medical device.

In another alternative, substantially all energy used for the medical device is stored in the at least one energy storage device. In yet another alternative, the energy used for the medical device is partly consumed to operate the medical device and partly stored in the at least one energy storage device.

The energy received by the internal energy receiver may be stabilized by a capacitor, before the energy is supplied directly or indirectly to the medical device.

The difference between the total amount of energy received by the internal energy receiver and the total amount of consumed and/or stored energy may be directly or indirectly measured over time, and the energy balance can then be determined based on a detected change in the total amount difference.

The energy received by the internal energy receiver may further be accumulated and stabilized in an energy stabilizing unit, before the energy is supplied to the medical device. In that case, the energy balance may be determined based on a detected change followed over time in the amount of consumed and/or stored energy. Further, the change in the amount of consumed and/or stored energy may be detected by determining over time the derivative of a measured electrical parameter related to the amount of consumed and/or stored energy, where the derivative at a first given moment is corresponding to the rate of the change at the first given moment, wherein the rate of change includes the direction and speed of the change. The derivative may further be determined based on a detected rate of change of the electrical parameter.

The energy received by the internal energy receiver may be supplied to the medical device with at least one constant voltage, wherein the constant voltage is created by a constant voltage circuitry. In that case, the energy may be supplied with at least two different voltages, including the at least one constant voltage.

The energy received by the internal energy receiver may also be supplied to the medical device with at least one constant current, wherein the constant current is created by a constant current circuitry. In that case, the energy may be supplied with at least two different currents including the at least one constant current.

The energy balance may also be determined based on a detected difference between the total amount of energy received by the internal energy receiver and the total amount of consumed and/or stored energy, the detected difference being related to the integral over time of at least one measured electrical parameter related to the energy balance. In that case, values of the electrical parameter may be plotted over time as a graph in a parameter-time diagram, and the integral can be determined from the size of the area beneath the plotted graph. The integral of the electrical parameter may relate to the energy balance as an accumulated difference between the total amount of energy received by the internal energy receiver and the total amount of consumed and/or stored energy.

The energy storage device in the medical device may include at least one of: a rechargeable battery, an accumulator or a capacitor. The energy stabilizing unit may include at least one of: an accumulator, a capacitor or a semiconductor adapted to stabilize the received energy.

When the energy received by the internal energy receiver is accumulated and stabilized in an energy stabilizing unit before energy is supplied to the medical device and/or energy storage device, the energy may be supplied to the medical device and/or energy storage device with at least one constant voltage, as maintained by a constant voltage circuitry. In that case, the medical device and energy storage device may be supplied with at least two different voltages, wherein at least one voltage is constant, maintained by the constant voltage circuitry.

Alternatively, when the energy received by the internal energy receiver is accumulated and stabilized in an energy stabilizing unit before energy is supplied to the medical device and/or energy storage device, the energy may be supplied to the medical device and/or energy storage device with at least one constant current, as maintained by a constant current circuitry. In that case, the medical device and energy storage device may be supplied with at least two different currents wherein at least one current is constant, maintained by the constant current circuitry.

The wireless energy may be initially transmitted according to a predetermined energy consumption plus storage rate. In that case, the transmission of wireless energy may be turned off when a predetermined total amount of energy has been transmitted. The energy received by the internal energy receiver may then also be accumulated and stabilized in an energy stabilizing unit before being consumed to operate the medical device and/or stored in the energy storage device until a predetermined total amount of energy has been consumed and/or stored.

Further, the wireless energy may be first transmitted with the predetermined energy rate, and then transmitted based on the energy balance which can be determined by detecting the total amount of accumulated energy in the energy stabilizing unit. Alternatively, the energy balance can be determined by detecting a change in the current amount of accumulated energy in the energy stabilizing unit. In yet another alternative, the energy balance, can be determined by detecting the direction and rate of change in the current amount of accumulated energy in the energy stabilizing unit.

The transmission of wireless energy may be controlled such that an energy reception rate in the internal energy receiver corresponds to the energy consumption and/or storage rate. In that case, the transmission of wireless energy may be turned off when a predetermined total amount of energy has been consumed.

The energy received by the internal energy receiver may be first accumulated and stabilized in an energy stabilizing unit, and then consumed or stored by the medical device until a predetermined total amount of energy has been consumed. In that case, the energy balance may be determined based on a detected total amount of accumulated energy in the energy stabilizing unit. Alternatively, the energy balance may be determined by detecting a change in the current amount of accumulated energy in the energy stabilizing unit. In yet another alternative, the energy balance may be determined by detecting the direction and rate of change in the current amount of accumulated energy in the energy stabilizing unit.

As mentioned in connection with FIG. 1, suitable sensors may be used for measuring certain characteristics of the medical device and/or detecting the current condition of the patient, somehow reflecting the required amount of energy needed for proper operation of the medical device. Thus, electrical and/or physical parameters of the medical device and/or physical parameters of the patient may be determined, and the energy can then be transmitted with a transmission rate which is determined based on the parameters. Further, the transmission of wireless energy may be controlled such that the total amount of transmitted energy is based on said parameters.

The energy received by the internal energy receiver may be first accumulated and stabilized in an energy stabilizing unit, and then consumed until a predetermined total amount of energy has been consumed. The transmission of wireless energy may further be controlled such that an energy reception rate at the internal energy receiver corresponds to a predetermined energy consumption rate.

Further, electrical and/or physical parameters of the medical device and/or physical parameters of the patient may be determined, in order to determine the total amount of transmitted energy based on the parameters. In that case, the energy received by the internal energy receiver may be first accumulated and stabilized in an energy stabilizing unit, and then consumed until a predetermined total amount of energy has been consumed.

The energy is stored in the energy storage device according to a predetermined storing rate. The transmission of wireless energy may then be turned off when a predetermined total amount of energy has been stored. The transmission of wireless energy can be further controlled such that an energy reception rate at the internal energy receiver corresponds to the predetermined storing rate.

The energy storage device of the medical device may comprise a first storage device and a second storage device, wherein the energy received by the internal energy receiver is first stored in the first storage device, and the energy is then supplied from the first storage device to the second storage device at a later stage.

When using the first and second storage devices in the energy storage device, the energy balance may be determined in different ways. Firstly, the energy balance may be determined by detecting the current amount of energy stored in the first storage device, and the transmission of wireless energy may then be controlled such that a storing rate in the second storage device corresponds to an energy reception rate in the internal energy receiver. Secondly, the energy balance may be determined based on a detected total amount of stored energy in the first storage device. Thirdly, the energy balance may be determined by detecting a change in the current amount of stored energy in the first storage device. Fourthly, the energy balance may be determined by detecting the direction and rate of change in the current amount of stored energy in the first storage device.

Stabilized energy may be first supplied from the first storage device to the second storage device with a constant current, as maintained by a constant current circuitry, until a measured voltage over the second storage device reaches a predetermined maximum voltage, and thereafter supplied from the first storage device to the second storage energy storage device with a constant voltage, as maintained by a constant voltage circuitry. In that case, the transmission of wireless energy may be turned off when a predetermined minimum rate of transmitted energy has been reached.

The transmission of energy may further be controlled such that the amount of energy received by the internal energy receiver corresponds to the amount of energy stored in the second storage device. In that case, the transmission of energy may be controlled such that an energy reception rate at the internal energy receiver corresponds to an energy storing rate in the second storage device. The transmission of energy may also be controlled such that a total amount of received energy at the internal energy receiver corresponds to a total amount of stored energy in the second storage device.

In the case when the transmission of wireless energy is turned off when a predetermined total amount of energy has been stored, electrical and/or physical parameters of the medical device and/or physical parameters of the patient may be determined during a first energy storing procedure, and the predetermined total amount of energy may be stored in a subsequent energy storing procedure based on the parameters.

When electrical and/or physical parameters of the medical device and/or physical parameters of the patient are determined, the energy may be stored in the energy storage device with a storing rate which is determined based on the parameters. In that case, a total amount of energy may be stored in the energy storage device, the total amount of energy being determined based on the parameters. The transmission of wireless energy may then be automatically turned off when the total amount of energy has been stored. The transmission of wireless energy may further be controlled such that an energy reception rate at the internal energy receiver corresponds to the storing rate.

When electrical and/or physical parameters of the medical device and/or physical parameters of the patient are determined, a total amount of energy may be stored in the energy storage device, the total amount of energy being determined based on said parameters. The transmission of energy may then be controlled such that the total amount of received energy at the internal energy receiver corresponds to the total amount of stored energy. Further, the transmission of wireless energy may be automatically turned off when the total amount of energy has been stored.

When the energy used for the medical device is partly consumed and partly stored, the transmission of wireless energy may be controlled based on a predetermined energy consumption rate and a predetermined energy storing rate. In that case, the transmission of energy may be turned off when a predetermined total amount of energy has been received for consumption and storage. The transmission of energy may also be turned off when a predetermined total amount of energy has been received for consumption and storage.

When electrical and/or physical parameters of the medical device and/or physical parameters of the patient are determined, the energy may be transmitted for consumption and storage according to a transmission rate per time unit which is determined based on said parameters. The total amount of transmitted energy may also be determined based on said parameters.

When electrical and/or physical parameters of the medical device and/or physical parameters of the patient are determined, the energy may be supplied from the energy storage device to the medical device for consumption with a supply rate which is determined based on said parameters. In that case, the total amount of energy supplied from the energy storage device to the medical device for consumption, may be based on said parameters.

When electrical and/or physical parameters of the medical device and/or physical parameters of the patient are determined, a total amount of energy may be supplied to the medical device for consumption from the energy storage device, where the total amount of supplied energy is determined based on the parameters.

When the energy received by the internal energy receiver is accumulated and stabilized in an energy stabilizing unit, the energy balance may be determined based on an accumulation rate in the energy stabilizing unit, such that a storing rate in the energy storage device corresponds to an energy reception rate in the internal energy receiver.

When a difference is detected between the total amount of energy received by the internal energy receiver and the total amount of consumed and/or stored energy, and the detected difference is related to the integral over time of at least one measured electrical parameter related to said energy balance, the integral may be determined for a monitored voltage and/or current related to the energy balance.

When the derivative is determined over time of a measured electrical parameter related to the amount of consumed and/or stored energy, the derivative may be determined for a monitored voltage and/or current related to the energy balance.

When using the first and second storage devices in the energy storage device, the second storage device may directly or indirectly supply energy to the medical device, wherein the change of the difference corresponds to a change of the amount of energy accumulated in the first storage unit. The energy balance may then be determined by detecting a change over time in the energy storing rate in the first storage device, the energy balance corresponding to the change. The change in the amount of stored energy may also be detected by determining over time the derivative of a measured electrical parameter indicating the amount of stored energy, the derivative corresponding to the change in the amount of stored energy. A rate of change of the electrical parameter may also be detected, the derivative being related to the change rate. The electrical parameter may be a measured voltage and/or current related to the energy balance.

The first storage device may include at least one of: a capacitor and a semiconductor, and the second storage device includes at least one of: a rechargeable battery, an accumulator and a capacitor.

As mentioned above, the wireless energy may be transmitted inductively from a primary coil in the external energy source to a secondary coil in the internal energy receiver. However, the wireless energy may also be transmitted non-inductively. For example, the wireless energy may be transmitted by means of sound or pressure variations, radio or light. The wireless energy may also be transmitted in pulses or waves and/or by means of an electric field.

When the wireless energy is transmitted from the external energy source to the internal energy receiver in pulses, the transmission of wireless energy may be controlled by adjusting the width of the pulses.

When the difference between the total amount of energy received by the internal energy receiver and the total amount of consumed energy is measured over time, directly or indirectly, the energy balance may be determined by detecting a change in the difference. In that case, the change in the amount of consumed energy may be detected by determining over time the derivative of a measured electrical parameter related to the amount of consumed energy, the derivative corresponding to the rate of the change in the amount of consumed energy, wherein the rate of change includes the direction and speed of the change. A rate of change of the electrical parameter may then be detected, the derivative being related to the detected change rate.

When using the first and second storage devices in the energy storage device, the first storage device may be adapted to be charged at a relatively higher energy charging rate as compared to the second storage device, thereby enabling a relatively faster charging. The first storage device may also be adapted to be charged at multiple individual charging occasions more frequently as compared to the second storage device, thereby providing relatively greater life-time in terms of charging occasions. The first storage device may comprise at least one capacitor. Normally, only the first storage may be charged and more often than needed for the second storage device.

When the second storage device needs to be charged, to reduce the time needed for charging, the first storage device is charged at multiple individual charging occasions, thereby leaving time in between the charging occasions for the first storage device to charge the second storage device at a relatively lower energy charging rate. When electrical parameters of the medical device are determined, the charging of the second storage device may be controlled based on the parameters. A constant current or stabilizing voltage circuitry may be used for storing energy in the second storage device.

The transmission of wireless energy from the external energy source may be controlled by applying to the external energy source electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

In that case, the frequency of the electrical pulses may be substantially constant when varying the first and/or second time intervals. When applying electrical pulses, the electrical pulses may remain unchanged, except for varying the first and/or second time intervals. The amplitude of the electrical pulses may be substantially constant when varying the first and/or second time intervals. Further, the electrical pulses may be varied by only varying the lengths of first time intervals between successive leading and trailing edges of the electrical pulses.

A train of two or more electrical pulses may be supplied in a row, wherein when applying the train of pulses, the train having a first electrical pulse at the start of the pulse train and having a second electrical pulse at the end of the pulse train, two or more pulse trains may be supplied in a row, wherein the lengths of the second time intervals between successive trailing edge of the second electrical pulse in a first pulse train and leading edge of the first electrical pulse of a second pulse train are varied.

When applying the electrical pulses, the electrical pulses may have a substantially constant current and a substantially constant voltage. The electrical pulses may also have a substantially constant current and a substantially constant voltage. Further, the electrical pulses may also have a substantially constant frequency. The electrical pulses within a pulse train may likewise have a substantially constant frequency.

When applying electrical pulses to the external energy source, the electrical pulses may generate an electromagnetic field over the external energy source, the electromagnetic field being varied by varying the first and second time intervals, and the electromagnetic field may induce electrical pulses in the internal energy receiver, the induced pulses carrying energy transmitted to the internal energy receiver. The wireless energy is then transmitted in a substantially purely inductive way from the external energy source to the internal energy receiver.

The electrical pulses may be released from the first electrical circuit with such a frequency and/or time period between leading edges of the consecutive pulses, so that when the lengths of the first and/or second time intervals are varied, the resulting transmitted energy are varied. When applying the electrical pulses, the electrical pulses may have a substantially constant frequency.

The circuit formed by the first electric circuit and the external energy source may have a first characteristic time period or first time constant, and when effectively varying the transmitted energy, such frequency time period may be in the range of the first characteristic time period or time constant or shorter.

While the invention has been described with reference to specific exemplary embodiments, the description is in general only intended to illustrate the inventive concept and should not be taken as limiting the scope of the invention. In particular, the skilled person will readily understand that the above-described embodiments and examples can be implemented both as a method and an apparatus. The present invention and various possible embodiments are generally defined by the following claims.

Description of Possible Implementation Examples

Figure 3:
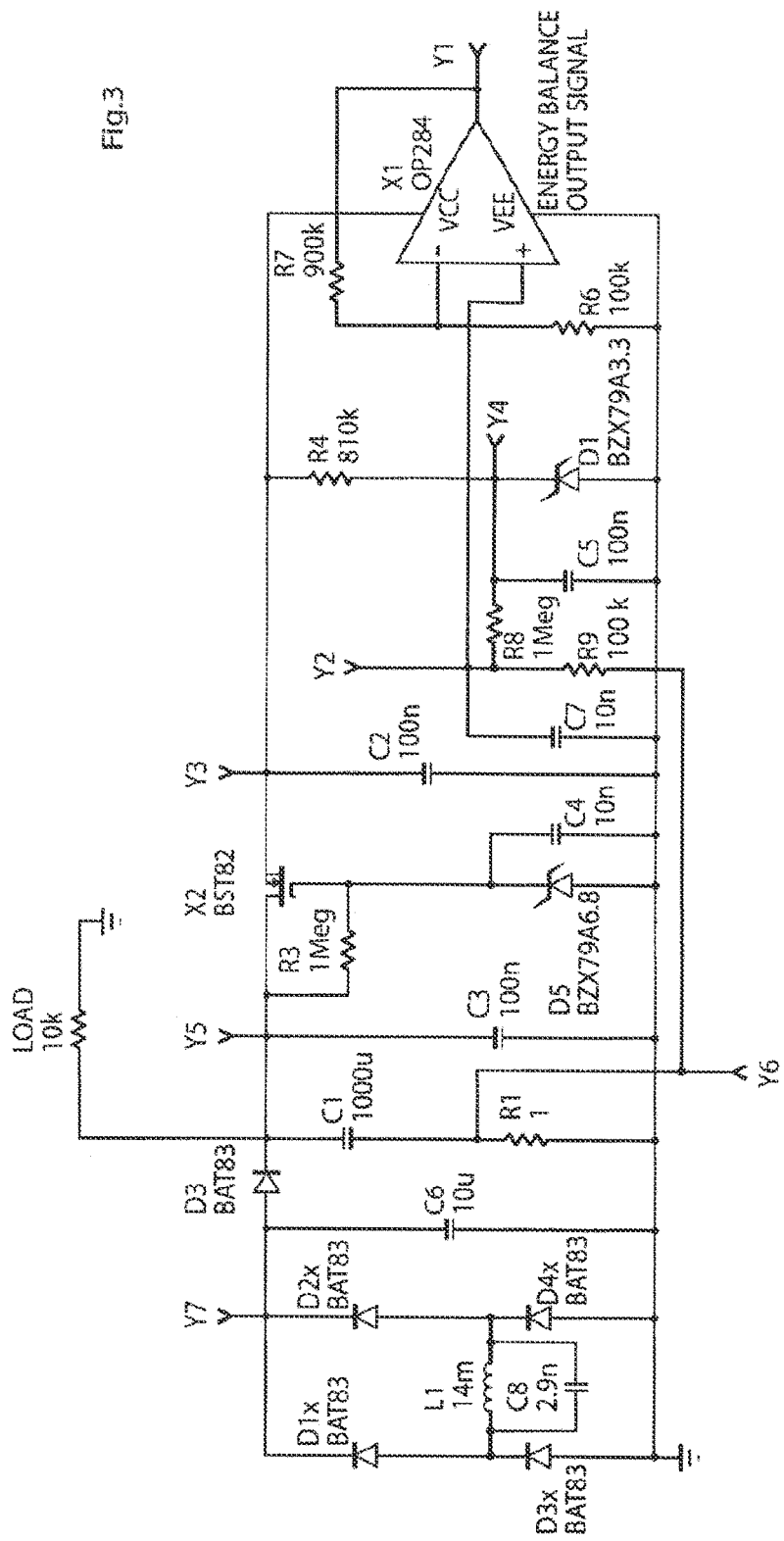
FIG. 3 is a schematic circuit diagram illustrating a proposed design of an apparatus for controlling transmission of wireless energy, according to a possible implementation example.

The schematic FIG. 3 shows a circuit diagram of one of the proposed designs of the invented apparatus for controlling transmission of wireless energy, or energy balance control system. The schematic shows the energy balance measuring circuit that has an output signal centered on 2.5V and that is proportional to the energy imbalance. A signal level at 2.5V means that energy balance exists, if the level drops below 2.5V energy is drawn from the power source in the implant and if the level rises above 2.5V energy is charged into the power source. The output signal from the circuit is typically feed to an A/D converter and converted into a digital format. The digital information can then be sent to the external transmitter allowing it to adjust the level of the transmitted power. Another possibility is to have a completely analog system that uses comparators comparing the energy balance level with certain maximum and minimum thresholds sending information to an external transmitter if the balance drifts out of the max/min window.

The schematic FIG. 3 shows a circuit implementation for a system that transfers power to the implant from outside of the body using inductive energy transfer. An inductive energy transfer system typically uses an external transmitting coil and an internal receiving coil. The receiving coil, L1, is included in the schematic FIG. 3; the transmitting parts of the system are excluded.

The implementation of the general concept of energy balance and the way the information is transmitted to the external energy transmitter can of course be implemented in numerous different ways. The schematic FIG. 3 and the above described method of evaluating and transmitting the information should only be regarded as examples of how to implement the control system.

Circuit Details

In the schematic FIG. 3 the symbols Y1, Y2, Y3 and so on symbolize test points within the circuit. References to the test points are found on the graphs in the diagrams following later in the text. The components in the diagram and their respective values are values that work in this particular implementation which of course is only one of an infinite number of possible design solutions.

Energy to power the circuit is received by the energy receiving coil L1. Energy to the implant is transmitted in this particular case at a frequency of 25 kHz. The energy balance output signal is present at test point Y1.

Figure 4:
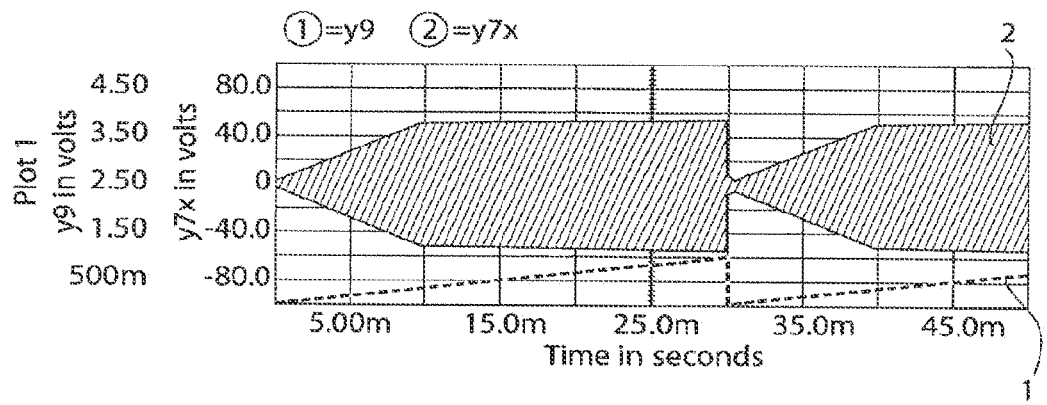

The diagram in FIG. 4 shows the voltage, Y7x, over the receiving coil L1 and the input power, Y9, received by the coil from the external transmitter. The power graph, Y9, is normalized and varies between 0-1 where 1 signifies maximum power and 0 no power; hence Y9 does not show the absolute value of the received power level. The power test point Y9 is not present in the schematic, it is an amplitude modulation signal on the transmitter signal power. In the diagram it can be seen that the Y7x voltage over the receiving coil L1 increases as the power from the external transmitter increases. When the Y7x voltage reaches the level where actual charging of the power source, C1, in the implant commences the Y7x level increases at a much slower rate as the input power is increased because of the load that the power source impart on the receiving coil.

Figure 5:
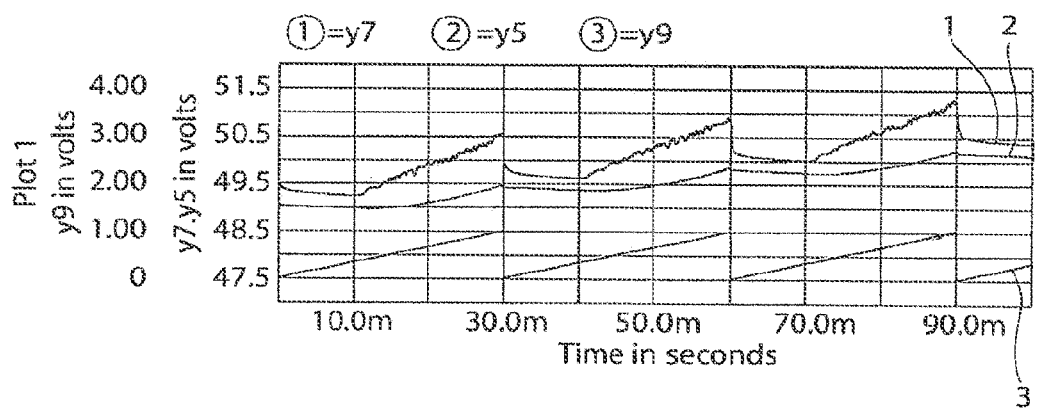

The receiving coil L1 is connected to a rectifying bridge with four Schottky diodes, D1x-D4x. The output voltage from the bridge, Y7, is shown in the diagram of FIG. 5. The capacitor C6 absorbs the high frequency charging currents from the bridge and together with the Schottky diode D3 prevents the 25 kHz energy transmission frequency from entering into the rest of the circuit. This is beneficial since the energy balance of the system is measured as the voltage across R1, which with out the C6-D3 combination would contain high level of 25 kHz alternating charge current. The power source in the implant is the capacitor C1. The capacitor C3 is a high frequency decoupling capacitor. The resistor named LOAD is the fictive load of the power source in the implant. The voltage over the power source. Y5, is also shown in the diagram of FIG. 5 together with the power graph Y9.

Figure 6:
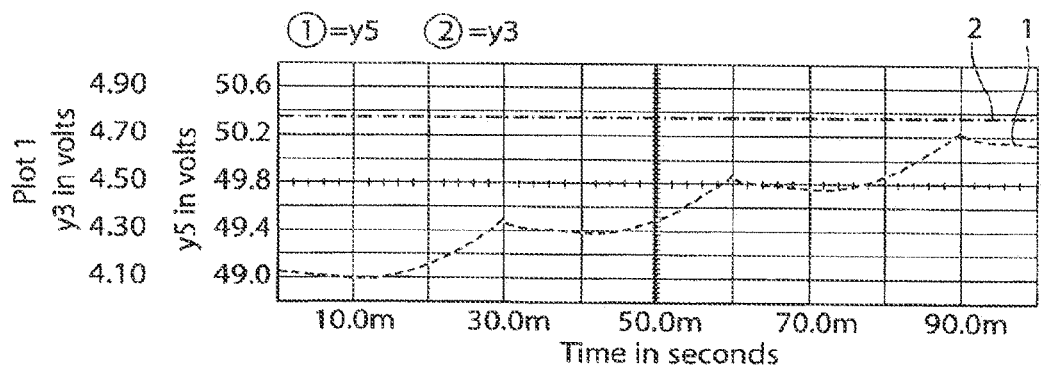

The voltage Y3 in the diagram of FIG. 6 is a stabilized voltage at about 4.8V used to power the operational amplifier X1. The Y3 voltage is stabilized by a fairly standard linear voltage regulator consisting of the MosFet X2, zenerdiode D5, capacitor C4 and resistor R3. The capacitor C2 is a high frequency decoupling capacitor. In the diagram of FIG. 6 the input voltage to the regulator is seen as Y5 and the output voltage is Y3.

The X1 operational amplifier is used to amplify the energy balance signal together with R6 and R7 that set the gain of the amplifier circuit to 10 times. The input signals to the circuit are shown in the diagram of FIG. 7. Y4 is fixed at a more or less constant level of approximately 2.74V by the zenerdiode D1. The voltage Y4 is shunted and high frequency filtered by the capacitor C5. A part of the DC voltage at Y4 is coupled into the Y2 voltage by the resistor R8 in order to center the Y1 output voltage at 2.5V when energy is balanced. The voltage Y2 is basically the same voltage as the voltage, Y6, over R1, only slightly high frequency filtered by R9 and C7 and shifted in DC level by the current going through R8. To compare Y6 and Y2 look in the diagram of FIG. 7.

The energy balance output signal of the circuit, Y1 in the diagram of FIG. 8, also closely correspond to the Y6 voltage. The Y1 voltage is an amplified, 10 times, and DC shifted to center around 2.5V instead of 0V version of the Y6 voltage. The higher signal level at Y1 and the DC center point around 2.5V is much easier to interface to for the circuits connected to the energy balance output signal.

The diagram of FIG. 9 shows the relationship between the energy balance signal Y1 and the actual voltage over the power source of the implant. The energy balance signal is the derivative of the voltage level over the power source, Y5. When the energy balance signal, Y1, is negative relative to 2.5V the voltage level, Y5, drops off and when the energy balance signal is positive relative to 2.5V the Y5 voltage increases. The more negative or positive relative to 2.5V the energy balance signal Y1 is the more rapidly the Y5 voltage over the power source increases or decreases.

The diagram of FIG. 10, of another circuit condition, perhaps even more clearly shows how the energy balance signal corresponds to the derivative of the Y5 voltage over the power source. The traces shows a situation where the energy put into the power source is held at a constant level and the load is varied between 5 mA and 30 mA in four discrete steps. During the first 25 ms the load is 30 mA, the following 25 ms it is 5 mA then followed by the same 30 mA and 5 mA sequence. When the Y5 voltage over the power source decreases at a constant level due to the 30 mA load the derivative level is at a constant level below 2.5V and when the Y5 voltage increases the derivative voltage is positive at a constant level.

The two diagrams of FIG. 11 show the relation ship between the energy balance signal Y1 and the energy imbalance in the circuit in a complex situation where both the load is varied and the amount of power put into the implant is varied. The two traces in the first diagram of FIG. 11 shows the charging current into the power source and the load current. The charging current is represented by the IY12 trace and the load current is the IY10 trace. The second diagram of FIG. 11 shows the Y1 voltage generated by the altering currents shown in the first diagram. When the amount of stored energy in the power source is changed due to the energy imbalance the derivative signal Y1 rapidly responds to the imbalance as shown in the diagram.

Figure 12:
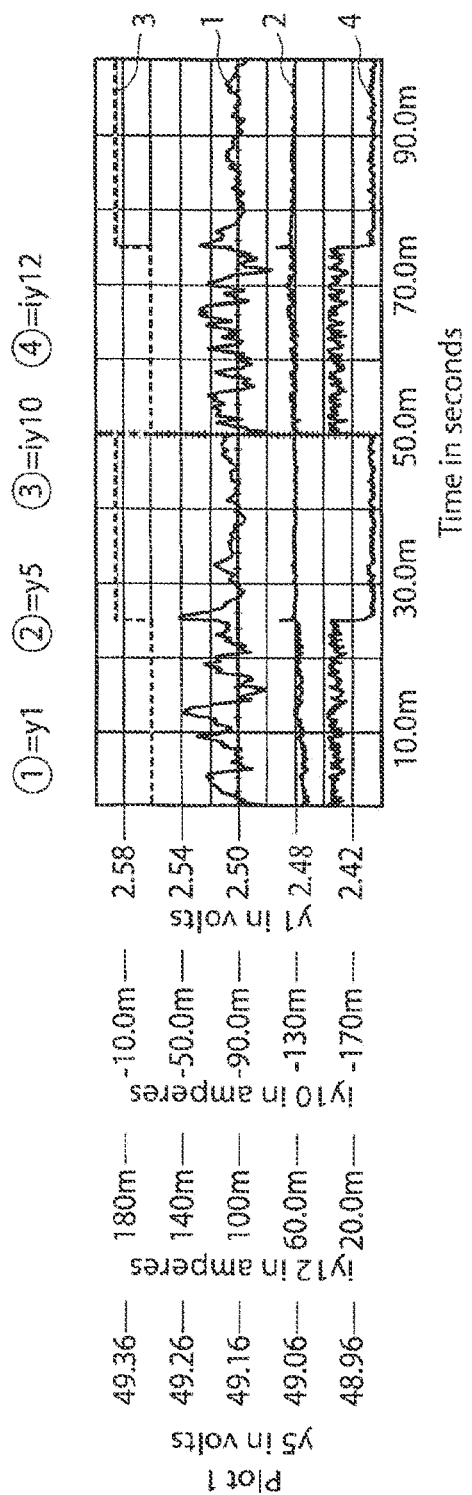

In a system where the energy balance signal is used as a feedback signal to an external power transmitter, enabling it to regulate the transmitted power according to the energy imbalance, it is possible to maintain an optimal energy balance and to keep the efficiency at maximum. The diagram of FIG. 12 shows the charging current into the power source and the load current, the charging current are represented by the IY12 trace and the load current is the IY10 trace, as well as the voltage level over the power source, Y5, and the energy balance signal Y1 in such a system. It can clearly be seen that this system rapidly responds to any load current changes by increasing the charging current. Only a small spike in the energy balance signal can be seen right at the edges where the load is rapidly changed due to the finite bandwidth of the feedback loop. Apart from those small spikes the energy is kept in perfect balance.

Figure 13A:
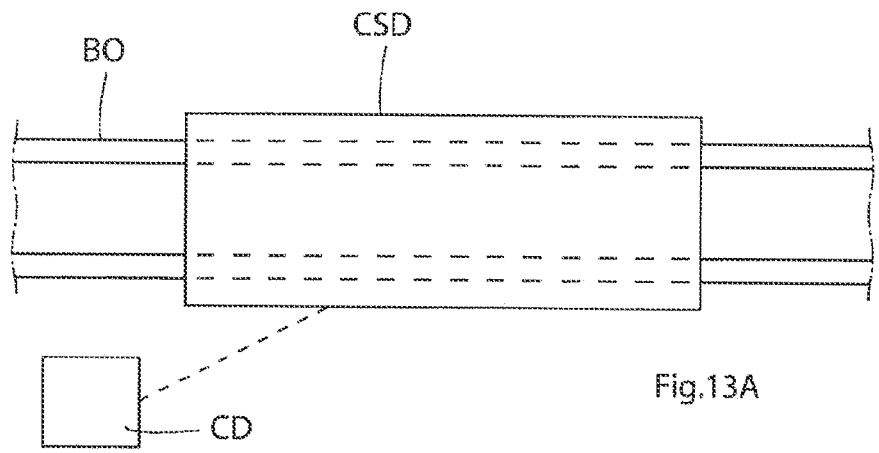
FIGS. 13a-13e schematically illustrate different states of operation of a general embodiment of an apparatus according to the present invention.
Figure 13B:
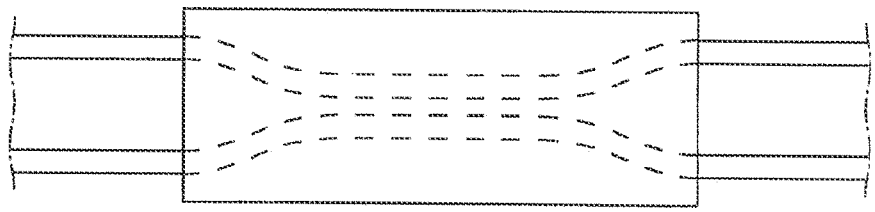
Figure 13C:
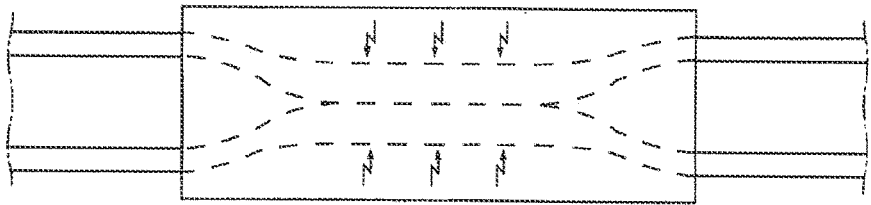

FIGS. 13a-13c schematically illustrate different states of operation of a generally designed apparatus according to the present invention, when the apparatus is applied on a wall portion of a bodily organ designated BO. The apparatus includes a constriction device and a stimulation device, which are designated CSD, and a control device designated CD for controlling the constriction and stimulation devices CSD. FIG. 9a shows the apparatus in an inactivation state, in which the constriction device does not constrict the organ BO and the stimulation device does not stimulate the organ BO. FIG. 13b shows the apparatus in a constriction state, in which the control device CD controls the constriction device to gently constrict the wall portion of the organ BO to a constricted state, in which the blood circulation in the constricted wall portion is substantially unrestricted and the flow in the lumen of the wall portion is restricted. FIG. 13c shows the apparatus in a stimulation state, in which the control device CD controls the stimulation device to stimulate different areas of the constricted wall portion, so that almost the entire wall portion of the organ BO contracts (thickens) and closes the lumen.

Figure 13D:
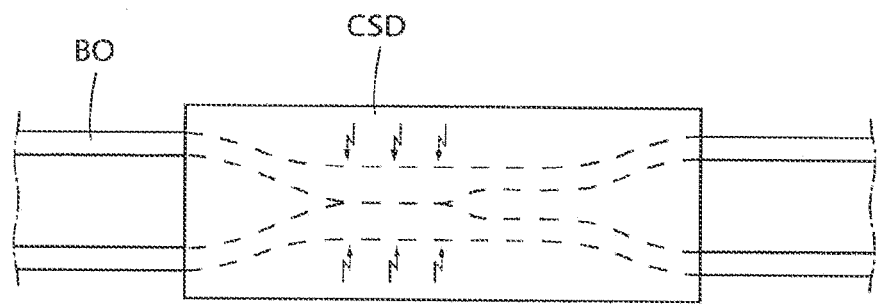
Figure 13E:
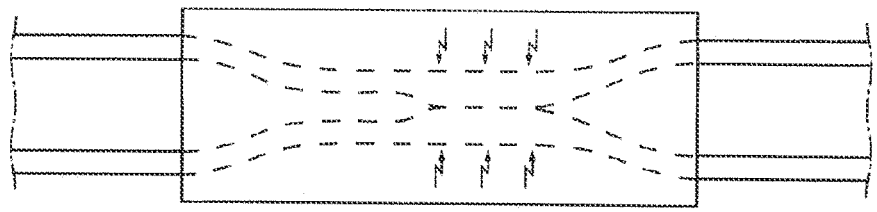

FIGS. 13d and 13e show how the stimulation of the constricted wall portion can be cyclically varied between a first stimulation mode, in which the left area of the wall portion (see FIG. 13d) is stimulated, while the right area of the wall portion is not stimulated, and a second stimulation mode, in which the right area of the wall portion (see FIG. 13e) is stimulated, while the left area of the wall portion is not stimulated, in order to maintain over time satisfactory blood circulation in the constricted wall portion.

It should be noted that the stimulation modes shown in FIGS. 13d and 13e only constitute a principle example of how the constricted wall portion of the organ BO may be stimulated. Thus, more than two different areas of the constricted wall portion may be simultaneously stimulated in cycles or successively stimulated. Also, groups of different areas of the constricted wall portion may be successively stimulated.

FIGS. 13f-13h illustrate different states of operation of a modification of the general embodiment shown in FIGS. 13a-13e, wherein the constriction and stimulation devices CSD include several separate constriction/stimulation elements, here three elements CSDE1. CSDE2 and CSDE3. FIG. 13f shows how the element CSDE1 in a first state of operation is activated to both constrict and stimulate the organ BO, so that the lumen of the organ BO is closed, whereas the other two elements CSDE2 and CSDE3 are inactivated. FIG. 13g shows how the element CSDE2 in a second following state of operation is activated, so that the lumen of the organ BO is closed, whereas the other two elements CSDE1 and CSDE3 are inactivated. FIG. 13h shows how the element CSDE3 in a following third state of operation is activated, so that the lumen of the organ BO is closed, whereas the other two elements CSDE1 and CSDE2 are inactivated. By shifting between the first, second and third states of operation, either randomly or in accordance with a predetermined sequence, different portions of the organ can by temporarily constricted and stimulated while maintaining the lumen of the organ closed, whereby the risk of injuring the organ is minimized. It is also possible to activate the elements CSDE1-CSDE3 successively along the lumen of the organ to move fluids and/or other bodily matter in the lumen.

FIGS. 13i-13k illustrate an alternative mode of operation of the modification of the general embodiment. Thus, FIG. 13i shows how the element CSDE1 in a first state of operation is activated to both constrict and stimulate the organ BO, so that the lumen of the organ BO is closed, whereas the other two elements CSDE2 and CSDE3 are activated to constrict but not stimulate the organ BO, so that the lumen of the organ BO is not completely closed where the elements CSDE2 and CSDE3 engage the organ BO. FIG. 13j shows how the element CSDE2 in a second following state of operation is activated to both constrict and stimulate the organ BO, so that the lumen of the organ BO is closed, whereas the other two elements CSDE1 and CSDE3 are activated to constrict but not stimulate the organ BO, so that the lumen of the organ BO is not completely closed where the elements CSDE1 and CSDE3 engage the organ BO. FIG. 13k shows how the element CSDE3 in a following third state of operation is activated to both constrict and stimulate the organ BO, so that the lumen of the organ BO is closed, whereas the other two elements CSDE1 and CSDE2 are activated to constrict but not stimulate the organ BO, so that the lumen of the organ BO is not completely closed where the elements CSDE1 and CSDE2 engage the organ BO. By shifting between the first, second and third states of operation, either randomly or in accordance with a predetermined sequence, different portions of the organ can by temporarily stimulated while maintaining the lumen of the organ closed, whereby the risk of injuring the organ is reduced. It is also possible to activate the stimulation of the elements CSDE1-CSDE3 successively along the lumen of the organ BO to move fluids and/or other bodily matter in the lumen.

Figure 14:
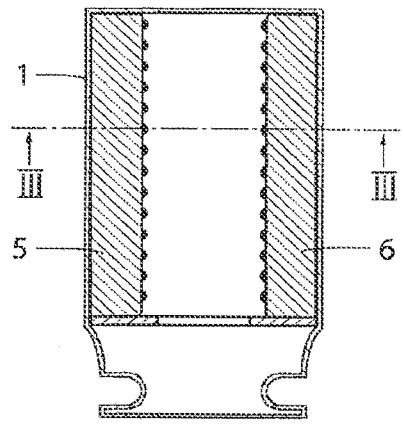
FIG. 14 is a longitudinal cross-section of a preferred embodiment of the apparatus according to the invention including a constriction device and an electric stimulation device.
Figure 15:
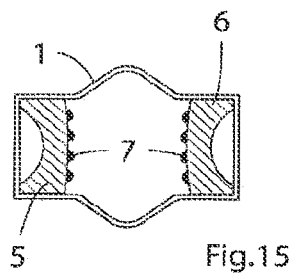
FIG. 15 is a cross-section along line in FIG. 10.
Figure 16:
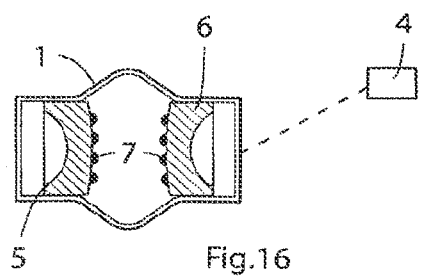
FIG. 16 is the same cross-section shown in FIG. 11, but with the apparatus in a different state of operation.

FIGS. 14-16 show basic components of an embodiment of the apparatus according to the invention for controlling a flow of fluid and/or other bodily matter in a lumen formed by a tissue wall of a patient's organ. The apparatus comprises a tubular housing 1 with open ends, a constriction device 2 arranged in the housing 1, a stimulation device 3 integrated in the constriction device 2, and a control device 4 (indicated in FIG. 16) for controlling the constriction and stimulation devices 2 and 3. The constriction device 2 has two elongate clamping elements 5, 6, which are radially movable in the tubular housing 1 towards and away from each other between retracted positions, see FIG. 15, and clamping positions, see FIG. 16. The stimulation device 3 includes a multiplicity of electrical elements 7 positioned on the clamping elements 5, 6, so that the electrical elements 7 on one of the clamping elements 5, 6 face the electrical elements 7 on the other clamping element. Thus, in this embodiment the constriction and stimulation devices form a constriction/stimulation unit, in which the constriction and stimulation devices are integrated in a single piece.

The constriction and stimulation devices may also be separate from each other. In this case, a structure may be provided for holding the electrical elements 7 in a fixed orientation relative to one another. Alternatively, the electrical elements 7 may include electrodes that are separately attached to the wall portion of the patient's organ.

Figure 17A:
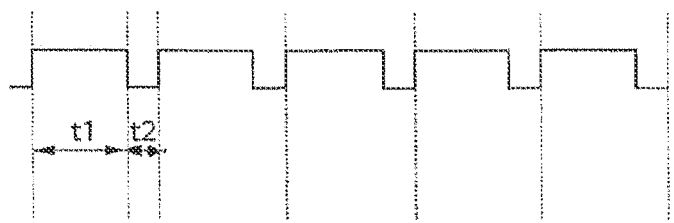
FIG. 17a is a diagram showing an example of pulses to be modified.

FIG. 17a shows an example of transmitted pulses, according to an embodiment of the present invention. The pulses have a constant frequency and amplitude. However, the relation between the times t1 and t2 varies.

Figure 17B:
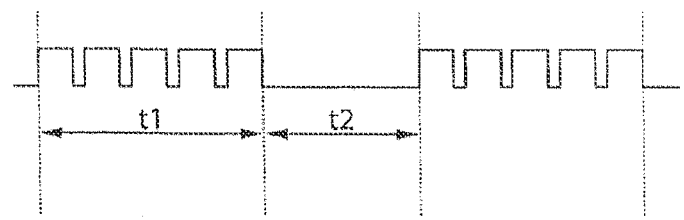
FIG. 17b is a diagram showing an example of a pulse train to be modified.

FIG. 17b shows another example of transmitted pulses, according to a second embodiment of the present invention. During the time t1 a train of pulses is transmitted, and during the time t2 no pulses are transmitted. The pulses have a constant frequency and amplitude. However, the relation between the times t1 and t2 varies.

What is claimed is:

1. An apparatus for controlling transmission of wireless energy supplied to an electrically operable medical device when implanted in a patient, comprising an external energy source, and an internal energy receiver, the apparatus being adapted to transmit said wireless energy from the external energy source located outside the patient which is received by the internal energy receiver located inside the patient, the internal energy receiver being connected to the medical device for directly or indirectly supplying received energy thereto, the apparatus being further adapted to:

determine an energy balance between the energy received by the internal energy receiver and the total energy used for the medical device, determine the energy balance, by an internal control unit or external control unit, during the transmission of wireless energy, transmit feed back information from inside the body to be able to control the wireless energy supply sent by the external energy source, and control the transmission of wireless energy from the external energy source, based on the determined energy balance, the apparatus is adapted to control the transmission of wireless energy in accordance with at least one of:
- an energy reception rate in the internal energy receiver compared to an total rate of used energy being consumption rate, storage rate or combined consumption and storage rate, and
- directly or indirectly measuring over time the difference between the total amount of energy received by the internal energy receiver and the total amount of used energy being consumed, stored or combined consumed and stored energy, and determining the energy balance based on at least one of: said difference and a detected change in said difference.

2. The apparatus according to claim 1, further comprising a primary coil in the external energy source and a secondary coil in the internal energy receiver, the apparatus further adapted to transmit the wireless energy inductively from the primary coil in the external energy source to the secondary coil in the internal energy receiver.

3. The apparatus according to claim 1, further adapted to detect at least at least one of:
- a change in said energy balance, and control the transmission of wireless energy based on said detected energy balance change, further adapted to decrease the amount of transmitted wireless energy if the detected energy balance change implies that the energy balance is increasing, or increase the amount of transmitted wireless energy if the detected energy balance change implies that the energy balance is decreasing, wherein the decrease/increase of energy transmission corresponds to a detected change rate, and
- a difference between energy received by said internal energy receiver and energy used for the medical device, and control the transmission of wireless energy based on said detected energy difference, further adapted to decrease the amount of transmitted wireless energy if the detected energy difference implies that the received energy is greater than the used energy, or increase the amount of transmitted wireless energy if the detected energy balance change implies that the energy balance is decreasing, wherein the decrease/increase of energy transmission corresponds to the magnitude of said detected energy difference.

4. The apparatus according to claim 3, further adapted to handle the energy used for the medical device in at least one of the following alternatives: a) consuming substantially all energy used for the medical device to operate the medical device, b) storing substantially all energy used for the medical device in at least one energy storage device and c) partly consuming the energy used for the medical device to operate the medical device and partly store the energy in said at least one energy storage device.

5. The apparatus according to claim 4, further comprising at least one energy stabilizing unit, the apparatus further adapted to consume or store the energy after being stabilized in the at least one energy stabilizing unit of the medical device.

6. The apparatus according to claim 5, adapted to transmit the wireless energy to be first transmitted with a predetermined energy rate, and then transmitted based on the energy balance, the apparatus adapted to determine by detecting the direction and rate of change in the current amount of accumulated energy in the energy stabilizing unit.

7. The apparatus according to claim 5, wherein the at least one energy stabilizing unit includes at least one of: an accumulator, a capacitor or a semiconductor adapted to stabilize the received energy.

8. The apparatus according to claim 4, further adapted to determine the energy balance based on a detected change followed over time in the amount of consumed, stored or consumed and stored energy.

9. The apparatus according to claim 8, further adapted to detect the change in the amount of consumed, stored or consumed and stored energy by determining over time the derivative of a measured electrical parameter related to said amount of consumed, stored or consumed and stored energy, the derivative at a first given moment corresponding to the rate of the change at the first given moment, wherein the rate of change includes the direction and speed of the change.

10. The apparatus according to claim 9, further adapted to determine said derivative based on a detected rate of change of the electrical parameter.

11. The apparatus according to claim 1, further adapted to supply the energy received by the internal energy receiver to the medical device with at least one of: at least one constant voltage, wherein the constant voltage is created by a comprised constant voltage circuitry, and at least one constant current, wherein the constant current is created by a comprised constant current circuitry.

12. The apparatus according to claim 11, further adapted to supply the energy with at least one of: at least two different voltages, including the at least one constant voltage, and at least two different currents, including said at least one constant current.

13. The apparatus according to claim 3, wherein said detected difference being related to the integral over time of at least one measured electrical parameter related to said energy balance, wherein said integral of the electrical parameter relates to the energy balance as an accumulated difference between the total amount of energy received by said internal energy receiver and the total amount of consumed energy, stored energy or consumed and stored energy.

14. The apparatus according to claim 13, further adapted to plot values of said electrical parameter over time as a graph in a parameter-time diagram, and determine said integral from the size of the area beneath the plotted graph.

15. The apparatus according to claim 3, further comprising an energy storage device comprising at least one of: a rechargeable battery, an accumulator or a capacitor.

16. The apparatus according to claim 1, further comprising:
- a first electric circuit to supply electrical pulses to the external transmitting device, said electrical pulses having leading and trailing edges, said transmitting device adapted to supply wireless energy, wherein
  - the electrical circuit being adapted to vary the lengths of at least one of:
    - first time intervals between successive leading and trailing edges of the electrical pulses, and
    - second time intervals between successive trailing and leading edges of the electrical pulses, wherein
  - the transmitted wireless energy, generated from the electrical pulses having a varied power, the power depending on the lengths of the first, second or first and second time intervals.

17. The apparatus according to claim 16, wherein the frequency of the electrical pulses is substantially constant when varying the first, second or first and second time intervals, wherein the amplitude of the electrical pulses is substantially constant when varying the first, second or first and second time intervals, when applying electrical pulses, so that the electrical pulses remain unchanged, except for varying the first, second or first and second time intervals.

18. The apparatus according to claim 16, further adapted to:
supply a train of two or more electrical pulses in a row, said train having a first electrical pulse at the start of the pulse train and having a second electrical pulse at the end of the pulse train, and
supply two or more pulse trains in a row, wherein the lengths of the second time intervals between successive trailing edge of the second electrical pulse in a first pulse train and leading edge of the first electrical pulse of a second pulse train are varied.

19. The apparatus according to claim 18, wherein, when applying electrical pulses, at least one of: the electrical pulses within the pulse trains, and the pulse trains themselves having at least one of: a substantially constant frequency, a substantially constant current and a substantially constant voltage.

20. The apparatus according to claim 16, further adapted to transmit the wireless energy in a substantially inductive way from the external energy source to the receiver and to release the electrical pulses from the first electrical circuit with at least one of: a frequency and time period between leading edges of the consecutive pulses, so that when the lengths of the first, second or first and second time intervals are varied, the resulting transmitted energy varied.

21. The apparatus according to claim 20, wherein the circuit formed by the first electric circuit and the external energy source has a first characteristic time period or first time constant, and when effectively varying the transmitted energy, such frequency time period is in the range of the first characteristic time period or time constant or shorter.

* * * * *